(12) United States Patent
Guillemont et al.

(10) Patent No.: US 8,802,671 B2
(45) Date of Patent: *Aug. 12, 2014

(54) QUINOLINE DERIVATIVES AS ANTIBACTERIAL AGENTS

(75) Inventors: Jérôme Emile Georges Guillemont, Ande (FR); Elisabeth Thérèse Jeanne Pasquier, Le Neubourg (FR); David Francis Alain Lançois, Louviers (FR); Koenraad Jozef Lodewijk Marcel Andries, Beerse (BE); Anil Koul, Berchem (BE); Leo Jacobus Jozef Backx, Arendonk (BE); Lieven Meerpoel, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 11/997,173

(22) PCT Filed: Jul. 31, 2006

(86) PCT No.: PCT/EP2006/064858
§ 371 (c)(1),
(2), (4) Date: Jan. 29, 2008

(87) PCT Pub. No.: WO2007/014941
PCT Pub. Date: Feb. 8, 2007

(65) Prior Publication Data
US 2008/0207687 A1 Aug. 28, 2008

(30) Foreign Application Priority Data
Aug. 3, 2005 (EP) .................................. 05107164

(51) Int. Cl.
*A61K 31/535* (2006.01)
(52) U.S. Cl.
USPC ....................................................... 514/235.2
(58) Field of Classification Search
None
See application file for complete search history.

(56) References Cited

U.S. PATENT DOCUMENTS 5,965,572 A * 10/1999 Ellis et al. ...................... 514/311
7,498,343 B2 * 3/2009 Van Gestel et al. ........... 514/312

FOREIGN PATENT DOCUMENTS

GB 807750 A 1/1959
WO WO 95/06047 A 3/1995

(Continued)

OTHER PUBLICATIONS

Schleicher et al (Int J Tuberc Lung Dis 7:1207-1208, 2003).*

(Continued)

Primary Examiner — Craig Ricci
(74) Attorney, Agent, or Firm — Thomas J. Dodd

(57) ABSTRACT

Use of a compound for the manufacture of a medicament for the treatment of a bacterial infection provided that the bacterial infection is other than a Mycobacterial infection, said compound being a compound of formula (I)

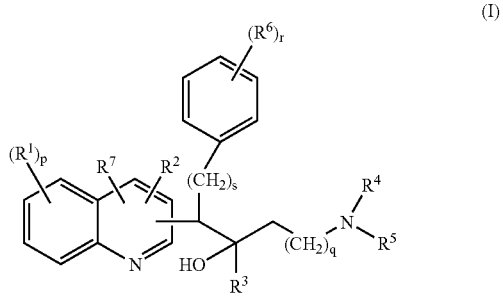

a pharmaceutically acceptable acid or base addition salt, a quaternary amine, a stereochemically isomeric form, a tautomeric form or a N-oxide form thereof, wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl; p is 1 to 3; s is 0 to 4; $R^2$ is hydrogen; halo; alkyl; hydroxy; mercapto; optionally substituted alkyloxy; alkyloxyalkyloxy; alkylthio; mono or di(alkyl)amino wherein alkyl may optionally be substituted; Ar; Het or a radical of formula

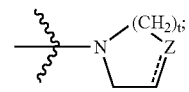

$R^3$ is alkyl, Ar, Ar-alkyl, Het or Het-alkyl; q is 0 to 4; $R^4$ and $R^5$ each independently are hydrogen, alkyl or benzyl; or $R^4$ and $R^5$ may be taken together including the N to which they are attached; $R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^6$ radicals may be taken together to form together with the phenyl ring to which they are attached a naphthyl; r is 1 to 5; $R^7$ is hydrogen, alkyl, Ar or Het; $R^8$ is hydrogen, alkyl, hydroxyl, aminocarbonyl, mono- or di(alkyl)aminocarbonyl, Ar, Het, alkyl substituted with one or two Het, alkyl substituted with one or two Ar, Het-C(=O)— or Ar—C(=O)—; provided that when the $R^3$ bearing radical is placed in position 3 of the quinoline moiety; $R^7$ is placed in position 4 and $R^2$ is placed in position 2 and represents hydrogen, hydroxy, mercapto, alkyloxy, alkyloxyalkyloxy, alkylthio, mono or di(alkyl)amino or a radical of formula

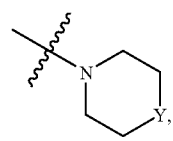

then s is 1 to 4.

11 Claims, No Drawings

(56) References Cited

FOREIGN PATENT DOCUMENTS

| WO | WO 00/34265 | * | 6/2000 | |
| WO | WO 2004/002490 | * | 1/2004 | ............. A61K 31/03 |
| WO | WO 2004/011436 | * | 2/2004 | ............ C07D 215/22 |
| WO | WO 20041011436 A | | 2/2004 | |
| WO | WO 2004/011436 | * | 5/2004 | ......... C07D 215/227 |
| WO | WO 2005/ 070430 | | 8/2005 | |
| WO | WO 2005/ 070924 | | 8/2005 | |
| WO | WO 2005/2075428 A | | 8/2005 | |
| WO | WO 2006/131519 A | | 12/2006 | |
| WO | WO 2007/014041 A2 | | 2/2007 | |

OTHER PUBLICATIONS

International Search Report dated Mar. 17, 2006 for related International Application No. PCT/EP2006/064858.

Andres, K. et al., "A Diarylquinoline Drug Active on the ATP Synthase of *Mycobacterium Tuberculosis*", Science, American Association for the Advancement of Science, US., vol. 307, Jan. 14, 2005, pp. 223-227, XP002358962, ISSN: 0036-8075.

Beller, M. et al., "Advances and Adentures in Amination Reactions of Olefins and Alkynes", Synlett, Thieme International, Stuttgart, DE, No. 10, pp. 1579-1594, XP001205461, ISSN: 0936-5214, age 1581-p. 1583.

Stella, V., et al. "Prodrugs: Do They Have Advantages in Clinical Practice?", Drugs vol. 29 (1985) pp. 455-473.

Stella, V. et al. "Prodrugs: The Control of Drug Delivery Via Bioreversible Chemical Modification" (1980) pp. 112-176.

Zurenko,G.E. et al. In Vitro Activities of U-100592 and U-100766, Novel Oxazolidinone Antibacterial Agents. *Antimicrob. Agents Chemother.* 40, pp. 839-845 (1996).

Rische, T., et al. Selective One-Pot Synthesis of Symmetrically and Unsymmetrically Substituted Amines via Rhodium Catalysed Multiple Alkylations of Ammonia or Primary Amines Under Hydroformylation Conditions, Tetrahedron, vol. 54, pp. 2723-2742 (1998).

* cited by examiner

QUINOLINE DERIVATIVES AS ANTIBACTERIAL AGENTS

CROSS REFERENCE TO RELATED APPLICATIONS

This application is a national stage application of Patent Application No. PCT/EP2006/064858, filed Jul. 31, 2006, which in turn claims the benefit of EPO Patent Application No. 05107164.5, filed Aug. 3, 2005. The complete disclosures of the aforementioned related patent applications are hereby incorporated herein by reference for all purposes.

The present invention relates to the use of quinoline derivatives for the manufacture of a medicament for the treatment of a bacterial infection.

Resistance to first-line antibiotic agents is an emerging problem. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection. Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially for the treatment of infections caused by resistant strains.

Substituted quinolines were already disclosed in U.S. Pat. No. 5,965,572 (The United States of America) for treating antibiotic resistant infections and in WO 00/34265 to inhibit the growth of bacterial microorganisms.

WO 2004/011436, WO2005/070924, WO2005/070430 and WO2005/075428 disclose substituted quinoline derivatives having activity against Mycobacteria, in particular against *Mycobacterium tuberculosis*. One particular compound of these substituted quinoline derivatives is described in Science (2005), 307, 223-227.

None of these publications disclose the use of the present substituted quinoline derivatives according to this invention.

SUMMARY OF THE INVENTION

The present invention relates to the use of a compound for the manufacture of a medicament for the treatment of a bacterial infection, said compound being a compound of formula (I)

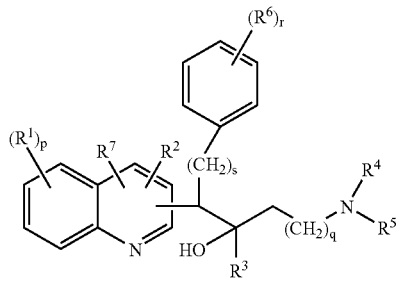

a pharmaceutically acceptable acid or base addition salt thereof, a quaternary amine thereof, a stereochemically isomeric form thereof, a tautomeric form thereof or a N-oxide form thereof, wherein:

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2 or 3;

s is an integer equal to zero, 1, 2, 3 or 4;

$R^2$ is hydrogen; halo; alkyl; hydroxy; mercapto; alkyloxy optionally substituted with amino or mono or di(alkyl)amino or a radical of formula

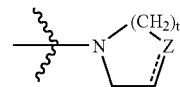

wherein Z is $CH_2$, CH—$R^8$, O, S, N—$R^8$ and t is an integer equal to 1 or 2 and the dotted line represents an optional bond; alkyloxyalkyloxy; alkylthio; mono or di(alkyl) amino wherein alkyl may optionally be substituted with one or two substituents each independently be selected from alkyloxy or Ar or Het or morpholinyl or 2-oxopyrrolidinyl; Ar; Het or a radical of formula

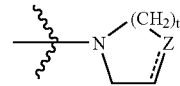

wherein Z is $CH_2$, CH—$R^8$, O, S, N—$R^8$; t is an integer equal to 1 or 2; and the dotted line represents an optional bond;

$R^3$ is alkyl, Ar, Ar-alkyl, Het or Het-alkyl;

q is an integer equal to zero, 1, 2, 3 or 4;

$R^4$ and $R^5$ each independently are hydrogen, alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings optionally being substituted with alkyl, halo, haloalkyl, hydroxy, alkyloxy, amino, mono- or dialkylamino, alkylthio, alkyloxyalkyl, alkylthioalkyl and pyrimidinyl;

$R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^6$ radicals may be taken together to form together with the phenyl ring to which they are attached a naphthyl;
r is an integer equal to 1, 2, 3, 4 or 5; and
$R^7$ is hydrogen, alkyl, Ar or Het;
$R^8$ is hydrogen, alkyl, hydroxyl, aminocarbonyl, mono- or di(alkyl)aminocarbonyl, Ar, Het, alkyl substituted with one or two Het, alkyl substituted with one or two Ar, Het-C(=O)— or Ar—C(=O)—;
alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo;
Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, alkylcarbonyl, aminocarbonyl, morpholinyl and mono- or dialkylaminocarbonyl;
Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, isoquinolinyl, 1,2,3,4-tetrahydroisoquinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents, each substituent independently selected from the group of halo, hydroxy, alkyl or alkyloxy;
halo is a substituent selected from the group of fluoro, chloro, bromo and iodo and
haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms;
provided that when the radical

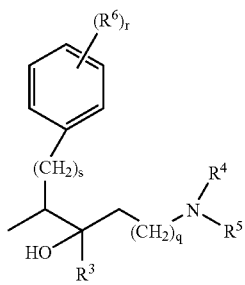

is placed in position 3 of the quinoline moiety; $R^7$ is placed in position 4 of the quinoline moiety and $R^2$ is placed in position 2 of the quinoline moiety and represents hydrogen, hydroxy, mercapto, alkyloxy, alkyloxyalkyloxy, alkylthio, mono or di(alkyl)amino or a radical of formula

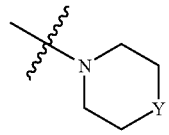

wherein Y is $CH_2$, O, S, NH or N-alkyl;
then s is 1, 2, 3 or 4; and
provided that the bacterial infection is other than a Mycobacterial infection.

The present invention also relates to a method of treating a bacterial infection provided that the bacterial infection is other than a Mycobacterial infection, in a mammal, in particular a warm-blooded mammal, more in particular a human, comprising administering an effective amount of a compound of the invention to the mammal.

DETAILED DESCRIPTION

In the framework of this application, alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo.

Preferably, alkyl is methyl, ethyl or cyclohexylmethyl. More preferably alkyl is $C_{1-6}$alkyl which, as a group or part of a group such as in haloalkyl, encompasses the straight and branched chain saturated hydrocarbon radicals having from 1 to 6 carbon atoms such as, methyl, ethyl, butyl, pentyl, hexyl, 2-methylbutyl and the like. A preferred subgroup of $C_{1-6}$alkyl is $C_{1-4}$alkyl which represents a straight or branched saturated hydrocarbon radical having from 1 to 4 carbon atoms such as for example methyl, ethyl, propyl, 2-methyl-ethyl and the like.

In the framework of this application, Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl. Preferably, Ar is naphthyl or phenyl, each optionally substituted with 1 or 2 halo substituents.

In the framework of this application, Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents, each substituent independently selected from the group of halo, hydroxy, alkyl or alkyloxy. Preferably Het is thienyl.

In the framework of this application, halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms. Preferably, halo is bromo, fluoro or chloro and preferably, haloalkyl is polyhalo$C_{1-6}$alkyl which is defined as mono- or polyhalosubstituted $C_{1-6}$alkyl, for example, methyl with one or more fluoro atoms, for example, difluoromethyl or trifluoromethyl, 1,1-difluoro-ethyl and the like. In case more than one halo atom is attached to an alkyl group within the definition of haloalkyl or polyhalo$C_{1-6}$alkyl, they may be the same or different.

In the framework of this application, the quinoline moiety is numbered as follows:

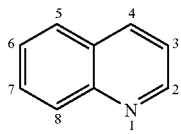

The

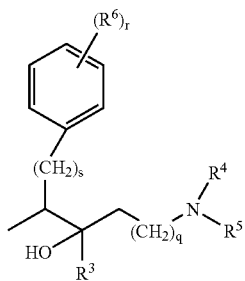

radical, $R^2$, $R^7$ and $R^1$ may be placed on any available position of the quinoline moiety.

In the definition of Het, it is meant to include all the possible isomeric forms of the heterocycles, for instance, pyrrolyl comprises 1H-pyrrolyl and 2H-pyrrolyl.

The Ar or Het listed in the definitions of the substituents of the compounds of formula (I) (see for instance $R^3$) as mentioned hereinbefore or hereinafter may be attached to the remainder of the molecule of formula (I) through any ring carbon or heteroatom as appropriate, if not otherwise specified. Thus, for example, when Het is imidazolyl, it may be 1-imidazolyl, 2-imidazolyl, 4-imidazolyl and the like.

Lines drawn from substituents into ring systems indicate that the bond may be attached to any of the suitable ring atoms.

The pharmaceutically acceptable acid addition salts are defined to comprise the therapeutically active non-toxic acid addition salt forms which the compounds according to formula (I) are able to form. Said acid addition salts can be obtained by treating the base form of the compounds according to formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to formula (I) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to formula (I) as well as the salts thereof, are able to form. Such solvates are, for example, hydrates and alcoholates.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylalkylhalide, alkylcarbonylhalide, Arcarbonylhalide, Hetalkylhalide or Hetcarbonylhalide, e.g. methyliodide or benzyliodide. Preferably, Het represents a monocyclic heterocycle selected from furanyl or thienyl; or a bicyclic heterocycle selected from benzofuranyl or benzothienyl; each monocyclic and bicyclic heterocycle may optionally be substituted with 1, 2 or 3 substituents, each substituent independently selected from the group of halo, alkyl and Ar. Preferably, the quaternizing agent is alkylhalide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. Preferably, the counterion is iodo. The counterion of choice can be introduced using ion exchange resins.

Compounds of formula (I) and some of the intermediate compounds invariably have at least two stereogenic centers in their structure which may lead to at least 4 stereochemically different structures.

The term "stereochemically isomeric forms" as used herein defines all possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of formula (I) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S—[R*,S*]. If "⟨" and "⊛" are used: the position of the highest priority substituent on the asymmetric carbon atom in the ring system having the lowest ring number, is arbitrarily always in the "⟨" position of the mean plane determined by the ring system. The position of the highest priority substituent on the other asymmetric carbon atom in the ring system relative to the position of the highest priority substituent on the reference atom is denominated "⟨", if it is on the same side of the mean plane determined by the ring system, or "⊛", if it is on the other side of the mean plane determined by the ring system.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (I) is for instance specified as (αS,βR), this means that the compound is substantially free of the (αR,βS) isomer.

The compounds of formula (I) may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of formula (I) are meant to comprise those compounds of formula (I) wherein e.g. an enol group is converted into a keto group (keto-enol tautomerism).

The N-oxide forms of the compounds according to formula (I) are meant to comprise those compounds of formula (I) wherein one or several nitrogen atoms are oxidized to the so-called N-oxide, particularly those N-oxides wherein the nitrogen of the amine radical is oxidized.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems*, 1985, pp. 112-176, and *Drugs*, 1985, 29, pp. 455-473.

Pro-drugs forms of the pharmacologically-active compounds according to the invention will generally be compounds according to formula (I), the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a $C_{1-6}$alkyl, phenyl, benzyl or one of the following groups:

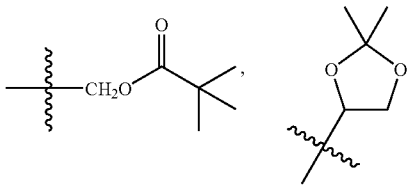

Amidated groups include groups of the formula —CONR$^y$R$^z$, wherein R$^y$ is H, $C_{1-6}$alkyl, phenyl or benzyl and R$^z$ is —OH, H, $C_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

Whenever used hereinafter, the term "compounds of formula (I)" is meant to also include their N-oxide forms, their salts, their quaternary amines, their tautomeric forms or their stereochemically isomeric forms. Of special interest are those compounds of formula (I) which are stereochemically pure.

An interesting embodiment of the present invention relates to those compounds of formula (I), the pharmaceutically acceptable acid or base addition salts thereof, the stereochemically isomeric forms thereof, the tautomeric forms thereof or the N-oxide forms thereof, wherein R$^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2 or 3;

s is an integer equal to zero, 1, 2, 3 or 4;

R$^2$ is hydrogen; halo; alkyl; hydroxy; mercapto; alkyloxy optionally substituted with amino or mono or di(alkyl) amino or a radical of formula

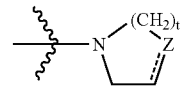

wherein Z is $CH_2$, CH—R$^8$, O, S, N—R$^8$ and t is an integer equal to 1 or 2 and the dotted line represents an optional bond; alkyloxyalkyloxy; alkylthio; mono or di(alkyl) amino wherein alkyl may optionally be substituted with one or two substituents each independently be selected from alkyloxy or Ar or Het or morpholinyl or 2-oxopyrrolidinyl; Het or a radical of formula

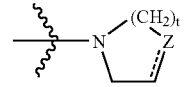

wherein Z is $CH_2$, CH—R$^8$, O, S, N—R$^8$; t is an integer equal to 1 or 2; and the dotted line represents an optional bond;

$R^3$ is alkyl, Ar, Ar-alkyl, Het or Het-alkyl;
q is an integer equal to zero, 1, 2, 3 or 4;
$R^4$ and $R^5$ each independently are hydrogen, alkyl or benzyl;
or
$R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, optionally substituted with alkyl, halo, haloalkyl, hydroxy, alkyloxy, amino, mono- or dialkylamino, alkylthio, alkyloxyalkyl, alkylthioalkyl and pyrimidinyl;
$R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl; or
two vicinal $R^6$ radicals may be taken together to form together with the phenyl ring to which they are attached a naphthyl;
r is an integer equal to 1, 2, 3, 4 or 5; and
$R^7$ is hydrogen, alkyl, Ar or Het;
$R^8$ is hydrogen, alkyl, aminocarbonyl, mono- or di(alkyl)aminocarbonyl, Ar, Het, alkyl substituted with one or two Het, alkyl substituted with one or two Ar, Het-C(=O)—
alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo;
Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, alkylcarbonyl, aminocarbonyl, morpholinyl and mono- or dialkylaminocarbonyl;
Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents, each substituent independently selected from the group of halo, hydroxy, alkyl or alkyloxy;
halo is a substituent selected from the group of fluoro, chloro, bromo and iodo and
haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms;

provided that when the radical

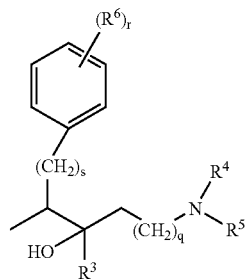

is placed in position 3 of the quinoline moiety; $R^7$ is placed in position 4 of the quinoline moiety and $R^2$ is placed in position 2 of the quinoline moiety and represents hydrogen, hydroxy, mercapto, alkyloxy, alkyloxyalkyloxy, alkylthio, mono or di(alkyl)amino or a radical of formula

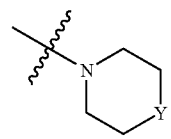

wherein Y is $CH_2$, O, S, NH or N-alkyl;
then s is 1, 2, 3 or 4.

Preferably, the invention relates to compounds of formula (I) or any subgroup thereof, as described hereinabove, provided that when the radical

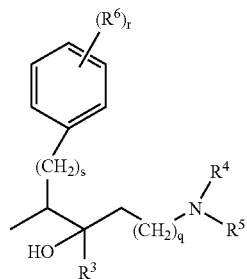

is placed in position 3 of the quinoline moiety; $R^7$ is placed in position 4 of the quinoline moiety and $R^2$ is placed in position 2 of the quinoline moiety, then s is 1, 2, 3 or 4.

Preferably, the invention relates to compounds of formula (I) or any subgroup thereof, as described hereinabove, provided that when the radical

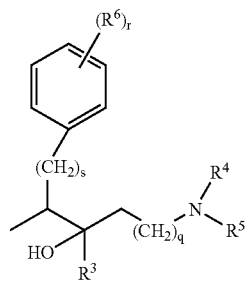

is placed in position 3 of the quinoline moiety; then s is 1, 2, 3 or 4.

Preferably, the invention relates to compounds of formula (I) or any subgroup thereof, as described hereinabove, provided that the radical

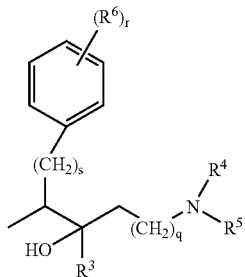

is not placed in position 3 of the quinoline moiety.

Preferably, the invention relates to compounds of formula (I) or any subgroup thereof, as described hereinabove, wherein the compounds have the following formula

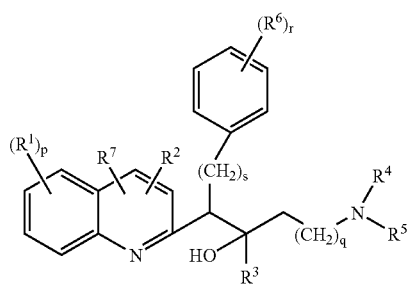
(I-a)

Preferably, the invention relates to compounds of formula (I-a-1) or any subgroup thereof, as described hereinabove

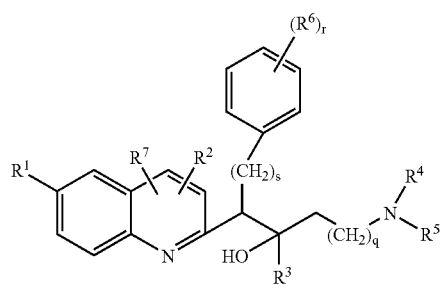
(I-a-1)

Preferably, the invention relates to compounds of formula (I-a-1-1) or any subgroup thereof, as described hereinabove

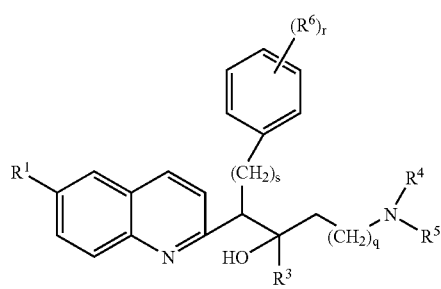
(I-a-1-1)

Preferably, the invention relates to compounds of formula (I) or any subgroup thereof, as described hereinabove, wherein the compounds have the following formula

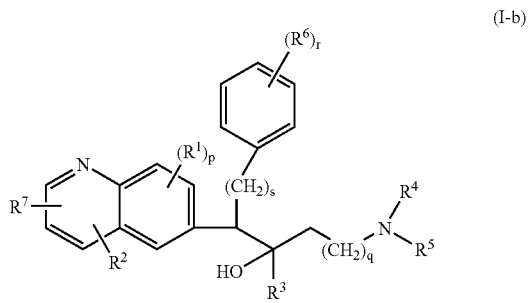
(I-b)

Preferably, the invention relates to compounds of formula (I) or any subgroup thereof, as described hereinabove, wherein the compounds have the following formula

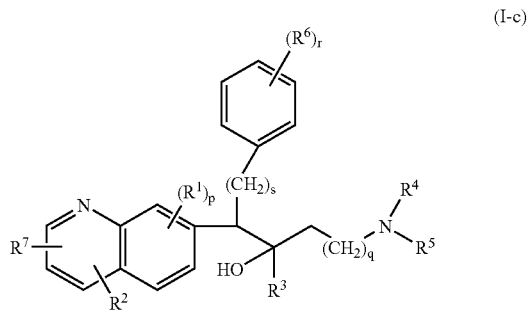
(I-c)

Preferably, the invention relates to compounds of formula (I) or any subgroup thereof, as described hereinabove, wherein:

$R^1$ is hydrogen, halo, cyano, Ar, Het, alkyl, or alkyloxy;
p is an integer equal to 1, 2, 3 or 4; in particular 1 or 2; more in particular 1;
s is an integer of 0 or 1;
$R^2$ is hydrogen; alkyl; hydroxy; alkyloxy optionally substituted with amino or mono or di(alkyl)amino or a radical of formula

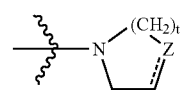

wherein Z is $CH_2$, $CH—R^{11}$, O, S, $N—R^{10}$ and t is an integer equal to 1 or 2 and the dotted line represents an optional bond; alkyloxyalkyloxy; alkylthio; mono or di(alkyl)amino; Ar; Het or a radical of formula

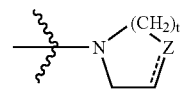

wherein Z is $CH_2$, $CH—R^{10}$, O, S, $N—R^{10}$; t is an integer equal to 1 or 2; and the dotted line represents an optional bond; in particular $R^2$ is hydrogen, hydroxy, alkyloxy, alkyloxyalkyloxy, alkylthio or a radical of formula

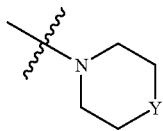

wherein Y is O; more in particular $R^2$ is hydrogen, halo or alkyl, even more in particular $R^2$ is hydrogen or alkyl;

$R^3$ is alkyl, Ar, Ar-alkyl or Het; in particular Ar;

q is an integer equal to zero, 1, 2, or 3; in particular 1;

$R^4$ and $R^5$ each independently are hydrogen, alkyl or benzyl; or $R^4$ and $R^5$ together and including the N to which they are attached may form a radical selected from the group of pyrrolidinyl, imidazolyl, triazolyl, piperidinyl, piperazinyl, pyrazinyl, morpholinyl and thiomorpholinyl, optionally substituted with alkyl and pyrimidinyl; in particular $R^4$ and $R^5$ are alkyl; more in particular $R^4$ and $R^5$ are $C_{1-6}$alkyl, preferably methyl;

$R^6$ is hydrogen, halo or alkyl; or two vicinal $R^6$ radicals may be taken together to form together with the phenyl ring to which they are attached a naphthyl;

r is an integer equal to 1; and $R^7$ is hydrogen or Ar; in particular hydrogen or phenyl;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy;

Ar is a homocycle selected from the group of phenyl, naphthyl, acenaphthyl, tetrahydronaphthyl, each optionally substituted with 1, 2 or 3 substituents, each substituent independently selected from the group of halo, haloalkyl, cyano, alkyloxy and morpholinyl;

Het is a monocyclic heterocycle selected from the group of N-phenoxypiperidinyl, furanyl, thienyl, pyridinyl, pyrimidinyl; or a bicyclic heterocycle selected from the group of benzothienyl, 2,3-dihydrobenzo[1,4]dioxinyl or benzo[1,3]-dioxolyl; each monocyclic and bicyclic heterocycle may optionally be substituted on a carbon atom with 1, 2 or 3 alkyl substituents; and halo is a substituent selected from the group of fluoro, chloro and bromo.

For compounds according to formula (I) or any subgroup thereof, as described hereinabove, preferably, $R^1$ is hydrogen, halo, Ar, Het, alkyl or alkyloxy. More preferably, $R^1$ is hydrogen, halo, Ar, alkyl or alkyloxy; even more preferably $R^1$ is hydrogen or halo, in particular halo. Most preferably, $R^1$ is bromo or chloro or $R^1$ is $C_{1-4}$alkyl.

For compounds according to formula (I) or any subgroup thereof, as described hereinabove, preferably, p is equal to 1 or 2. More preferably, p is equal to 1.

For compounds according to formula (I) or any subgroup thereof, as described hereinabove, preferably, $R^2$ is hydrogen; halo; alkyl; hydroxy; mercapto; alkyloxy optionally substituted with amino or mono or di(alkyl)amino or a radical of formula

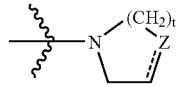

wherein Z is $CH_2$, CH—$R^8$, O, S, N—$R^8$ and t is an integer equal to 1 or 2 and the dotted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Het or a radical of formula

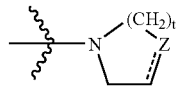

wherein Z is $CH_2$, CH—$R^8$, O, S, N—$R^8$; t is an integer equal to 1 or 2; and the dotted line represents an optional bond.

Also, an interesting group of compounds of formula (I) or any subgroup thereof, as described hereinabove, are those compounds wherein $R^2$ is hydrogen; alkyl; alkyloxy optionally substituted with amino or mono or di(alkyl)amino or a radical of formula

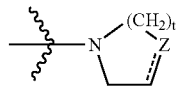

wherein Z is $CH_2$, CH—$R^{10}$, O, S, N—$R^{10}$ and t is an integer equal to 1 or 2 and the dotted line represents an optional bond; mono or di(alkyl)amino; Ar; Het or a radical of formula

wherein Z is $CH_2$, CH—$R^{10}$, O, S, N—$R^{10}$; t is an integer equal to 1 or 2; and the dotted line represents an optional bond. More preferably, $R^2$ is hydrogen, halo, alkyl, alkyloxy or alkylthio. Even more preferably, $R^2$ is hydrogen, halo or $C_{1-6}$alkyl (e.g. ethyl). Most preferably, $R^2$ is hydrogen or $C_{1-6}$alkyl (e.g. ethyl) or $R^2$ is hydrogen or halo or $R^2$ is $C_{1-4}$alkyloxy.

For compounds according to formula (I) or any subgroup thereof, as described hereinabove, preferably, $R^3$ is naphthyl, phenyl or Het, each optionally substituted with 1 or 2 substituents, that substituent preferably being a halo or haloalkyl, most preferably being a halo. More preferably, $R^3$ is optionally substituted naphthyl or optionally substituted phenyl. Most preferably, $R^3$ is naphthyl or optionally substituted phenyl (e.g. 3-halophenyl or 3,5-dihalophenyl).

For compounds according to formula (I) or any subgroup thereof, as described hereinabove, q is equal to zero, 1 or 2. More preferably, q is equal to 1 or q is equal to 3.

For compounds according to formula (I) or any subgroup thereof, as described hereinabove, $R^4$ and $R^5$ each independently are hydrogen or alkyl, more preferably hydrogen, or $C_{1-6}$alkyl, e.g. methyl or ethyl, most preferably $C_{1-6}$alkyl, e.g. methyl.

For compounds according to formula (I) or any subgroup thereof, as described hereinabove, $R^4$ and $R^5$ together and including the N to which they are attached form a radical selected from the group of imidazolyl, triazolyl, piperidinyl, piperazinyl and thiomorpholinyl, optionally substituted with alkyl, halo, haloalkyl, hydroxy, alkyloxy, alkylthio, alkyloxyalkyl or alkylthioalkyl, preferably substituted with alkyl, most preferably substituted with methyl or ethyl.

For compounds according to formula (I) or any subgroup thereof, as described hereinabove, $R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl. More preferably, $R^6$ is hydrogen, alkyl or halo. Most preferably, $R^6$ is hydrogen. Preferably r is 1 or 2. More preferably, r is 1.

For compounds according to formula (I) or any subgroup thereof, as described hereinabove, preferably, $R^7$ is hydrogen or alkyl, more preferably hydrogen or $C_{1-6}$alkyl.

For compounds according to formula (I) or any subgroup thereof, as described hereinabove, preferably, $R^8$ is hydrogen, alkyl, aminocarbonyl, mono- or di(alkyl)aminocarbonyl, Ar, Het, alkyl substituted with one or two Het, alkyl substituted with one or two Ar, Het-C(=O)—.

For compounds according to formula (I) or any subgroup thereof, as described hereinabove, preferably, s is an integer equal to 0 or 1.

An interesting group of compounds of formula (I) or any subgroup thereof, as defined hereinabove, are those compounds wherein
$R^1$ is hydrogen or halo, in particular halo, e.g. bromo;
p is equal to 1;
s is equal to 0 or 1;
$R^2$ is hydrogen, halo, alkyl or alkyloxy; in particular hydrogen, $C_{1-4}$alkyl or $C_{1-4}$alkyloxy;
$R^3$ is optionally substituted phenyl or optionally substituted naphthyl, in particular 3-halophenyl, 3,5-dihalophenyl or naphthyl;
$R^4$ and $R^5$ are $C_{1-6}$alkyl, in particular methyl.
$R^6$ is hydrogen and r is 1.
$R^7$ is hydrogen or alkyl, in particular hydrogen, methyl or ethyl.

An interesting embodiment is the use of a compound of formula (I) or any subgroup thereof, as described hereinabove, for the manufacture of a medicament for the treatment of an infection with a gram-positive and/or a gram-negative bacterium.

An interesting embodiment is the use of a compound of formula (I) or any subgroup thereof, as described hereinabove, for the manufacture of a medicament for the treatment of an infection with a gram-positive bacterium.

An interesting embodiment is the use of the compounds of formula (I) or any subgroup thereof, as described hereinabove, for the manufacture of a medicament for the treatment of an infection with a gram-negative bacterium.

An interesting embodiment is the use of a compound of formula (I) or any subgroup thereof, as described hereinabove, for the manufacture of a medicament for the treatment of a bacterial infection wherein the compound of formula (I) has a $IC_{90}$<15 μl/ml against at least one bacterium, in particular a gram-positive bacterium, preferably a $IC_{90}$<10 μl/ml, more preferably a $IC_{90}$<5 μl/ml; the $IC_{90}$ value being determined as described hereinafter.

Preferably, in the compounds of formula (I) or any subgroup thereof as mentioned hereinbefore as interesting embodiment, the term "alkyl" represents $C_{1-6}$alkyl, more preferably $C_{1-4}$alkyl.

Preferred compounds of the present invention are compounds 1, 2, 5, 6, 8, 9, 10, 11, 12 and 13 as described hereinafter in the experimental part, a pharmaceutically acceptable acid or base addition salt thereof, a quaternary amine thereof, a stereochemically isomeric form thereof, a tautomeric form thereof or a N-oxide form thereof.

The present invention also relates to a compound selected from

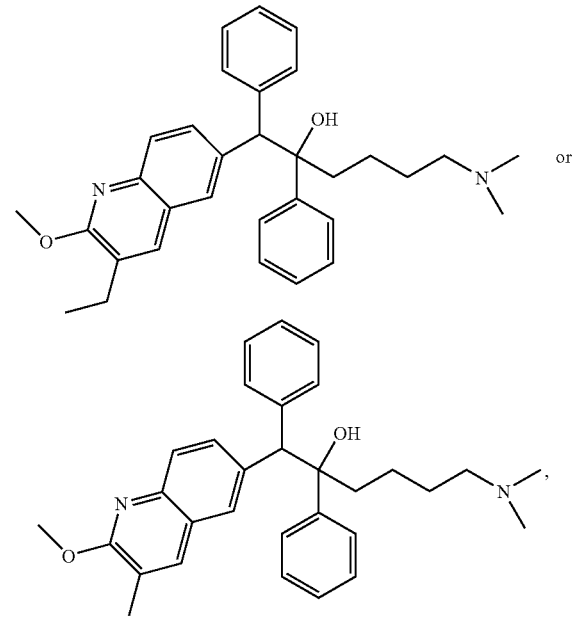

a pharmaceutically acceptable acid or base addition salt thereof, a quaternary amine thereof, a stereochemically isomeric form thereof, a tautomeric form thereof or a N-oxide form thereof.

In general, bacterial pathogens may be classified as either gram-positive or gram-negative pathogens. Antibiotic compounds with activity against both gram-positive and gram-negative pathogens are generally regarded as having a broad spectrum of activity. The compounds of the present invention are regarded as active against gram-positive and/or gram-negative bacterial pathogens. In particular, the present compounds are active against at least one gram-positive bacterium, preferably against several gram-positive bacteria, more preferably against one or more gram-positive bacteria and/or one or more gram-negative bacteria.

The present compounds have bactericidal or bacteriostatic activity.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogens*; Bacilli, for example *Bacillus subtilis; Listeria*, for example *Listeria monocytogenes; Haemophilus*, for example *H. influenza; Moraxella*, for example *M. catarrhalis; Pseudomonas*, for example *Pseudomonas aeruginosa*; and *Escherichia*, for example *E. coli*. Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against *Staphylococcus aureus*, including resistant *Sta-*

*phylococcus aureus* such as for example methicillin resistant *Staphylococcus aureus* (MRSA), and *Streptococcus pneumoniae*.

In particular, the compounds of the present invention are active on those bacteria of which the viability depends on proper functioning of F1F0 ATP synthase. Without being bound to any theory, it is taught that the activity of the present compounds lies in inhibition of the F1F0 ATP synthase, in particular the inhibition of the F0 complex of the F1F0 ATP synthase, more in particular the inhibition of subunit c of the F0 complex of the F1F0 ATP synthase, leading to killing of the bacteria by depletion of the cellular ATP levels of the bacteria.

Whenever used hereinbefore or hereinafter, that the compounds can treat a bacterial infection it is meant that the compounds can treat an infection with one or more bacterial strains.

Whenever used hereinbefore or hereinafter, that the bacterial infection is other than a Mycobacterial infection it is meant that the bacterial infection is other than an infection with one or more Mycobacteria strains.

The exact dosage and frequency of administration of the present compounds depends on the particular compound of formula (I) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compound of the present invention may be administered in a pharmaceutically acceptable form optionally in a pharmaceutically acceptable carrier. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, rectal, and oral administration. The specific dosage of antibacterial to be administered, as well as the duration of treatment, may be adjusted as needed.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Given the fact that the compounds of formula (I) are active against bacterial infections, the present compounds may be combined with other antibacterial agents in order to effectively combat bacterial infections.

Therefore, the present invention also relates to a combination of (a) a compound of formula (I), and (b) one or more other antibacterial agents provided that the one or more other antibacterial agents are other than antimycobacterial agents.

The present invention also relates to a combination of (a) a compound of formula (I), and (b) one or more other antibacterial agents provided that the one or more other antibacterial agents are other than antimycobacterial agents, for use as a medicine.

A pharmaceutical composition comprising a pharmaceutically acceptable carrier and, as active ingredient, a therapeutically effective amount of (a) a compound of formula (I), and (b) one or more other antibacterial agents provided that the one or more other antibacterial agents are other than antimycobacterial agents, is also comprised by the present invention.

The present invention also relates to the use of a combination or pharmaceutical composition as defined above for the treatment of a bacterial infection.

The present pharmaceutical composition may have various pharmaceutical forms for administration purposes. As appropriate compositions there may be cited all compositions usually employed for systemically administering drugs. To prepare the pharmaceutical compositions of this invention, an effective amount of the particular compounds, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral unit dosage forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredients, and, from 1 to 99.95% by weight, more preferably from 30 to 99.9 weight % of a pharmaceutically acceptable carrier, all percentages being based on the total composition.

The weight to weight ratio's of the compound of formula (I) and (b) the other antibacterial agent(s) when given as a combination may be determined by the person skilled in the art. Said ratio and the exact dosage and frequency of administration depends on the particular compound of formula (I) and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention.

The compounds of formula (I) and the one or more other antibacterial agents may be combined in a single preparation or they may be formulated in separate preparations so that they can be administered simultaneously, separately or sequentially. Thus, the present invention also relates to a product containing (a) a compound of formula (I), and (b) one or more other antibacterial agents provided that the one or more other antibacterial agents are other than antimycobacterial agents, as a combined preparation for simultaneous, separate or sequential use in the treatment of a bacterial infection.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the bacterial disease indicated.

The other antibacterial agents which may be combined with the compounds of formula (I) are antibacterial agents known in the art. The other antibacterial agents comprise antibiotics of the β-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes.

Specific antibiotics which may be combined with the present compounds of formula (I) are for example benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, siccanin.

General Preparation

The compounds according to the invention can generally be prepared by a succession of steps, each of which is known to the skilled person.

Compounds of formula (I) can be prepared by reacting an intermediate of formula (II) with an intermediate of formula (III) in the presence of a suitable coupling agent, such as for example n-butyl lithium, secBuLi, and in the presence of a suitable solvent, such as for example tetrahydrofuran, and optionally in the presence of a suitable base, such as for example 2,2,6,6-tetramethylpiperidine, $NH(CH_2CH_2CH_3)_2$, N,N-diisopropylamine or trimethylethylenediamine.

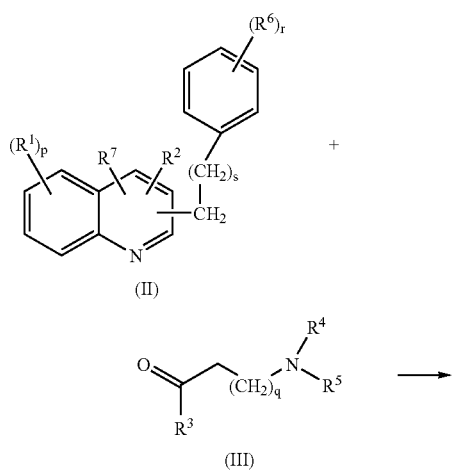

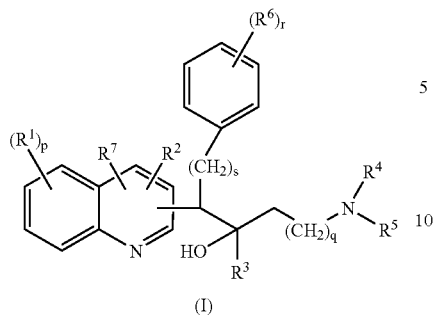

(I)

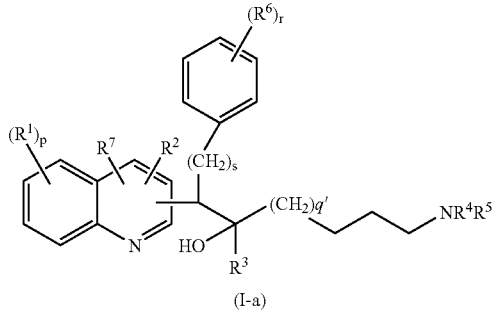

(I-a)

In the above reaction, the obtained compound of formula (I) can be isolated, and, if necessary, purified according to methodologies generally known in the art such as, for example, extraction, crystallization, distillation, trituration and chromatography. In case the compound of formula (I) crystallizes out, it can be isolated by filtration. Otherwise, crystallization can be caused by the addition of an appropriate solvent, such as for example water; acetonitrile; an alcohol, such as for example methanol, ethanol; and combinations of said solvents. Alternatively, the reaction mixture can also be evaporated to dryness, followed by purification of the residue by chromatography (e.g. reverse phase HPLC, flash chromatography and the like). The reaction mixture can also be purified by chromatography without previously evaporating the solvent. The compound of formula (I) can also be isolated by evaporation of the solvent followed by recrystallisation in an appropriate solvent, such as for example water; acetonitrile; an alcohol, such as for example methanol; and combinations of said solvents. The person skilled in the art will recognise which method should be used, which solvent is the most appropriate to use or it belongs to routine experimentation to find the most suitable isolation method.

The compounds of formula (I) wherein q is equal to 2, 3 or 4, said compounds being represented by formula (I-a), can also be prepared by reacting an intermediate of formula (XVIII) wherein q' is 0, 1 or 2, with a primary or secondary amine $HNR^4R^5$ in the presence of a suitable catalyst, such as for example $Rh(cod)_2BF_4$, optionally in the presence of a second catalyst (for the reduction), such as for example $Ir(cod)_2BF_4$, in the presence of a suitable ligand, such as for example Xantphos, in a suitable solvent, such as for example tetrahydrofuran and an alcohol, e.g. methanol, in the presence of CO and $H_2$ (under pressure) at elevated temperature. This reaction is preferably done for intermediates of formula (XVIII) wherein q' is 1.

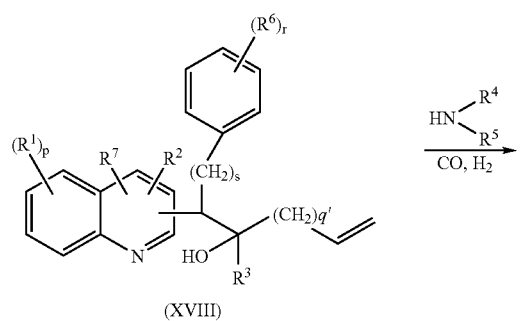

(XVIII)

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^1$ represents halo, can be converted into a compound of formula (I) wherein $R^1$ represents Het, e.g. pyridyl, by reaction with

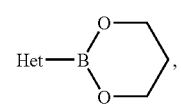

in the presence of a suitable catalyst, such as for example $Pd(PPh_3)_4$, a suitable solvent, such as for example dimethylether or an alcohol, e.g. methanol and the like, and a suitable base, such as for example disodium carbonate or dipotassium carbonate.

Compounds of formula (I) wherein $R^1$ represents halo, can also be converted into a compound of formula (I) wherein $R^1$ represents methyl, by reaction with $Sn(CH_3)_4$ in the presence of a suitable catalyst, such as for example $Pd(PPh_3)_4$, a suitable solvent, such as for example toluene.

Some of the compounds of formula (I) and some of the intermediates in the present invention may consist of a mixture of stereochemically isomeric forms. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase or supercritical fluid chromatography.

It is to be understood that in the above or the following preparations, the reaction products may be isolated from the reaction medium and, if necessary, further purified according to methodologies generally known in the art such as, for example, extraction, crystallization, distillation, trituration and chromatography.

Some of the intermediates and starting materials are known compounds and may be commercially available or may be prepared according to art-known procedures or procedures described in WO2004/011436, which is incorporated herein by reference.

Intermediates of formula (II) wherein the

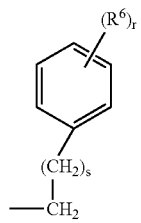

radical is placed in position 2 of the quinoline ring, s is an integer equal to 1 and position 4 of the quinoline ring is unsubstituted, said intermediates being represented by formula (II-a), can be prepared by reacting an intermediate of formula (IV) with phenyloxybenzene in the presence of ethyl acetate.

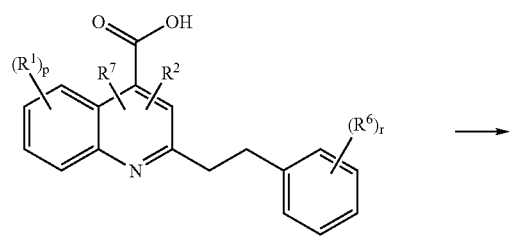

(IV)

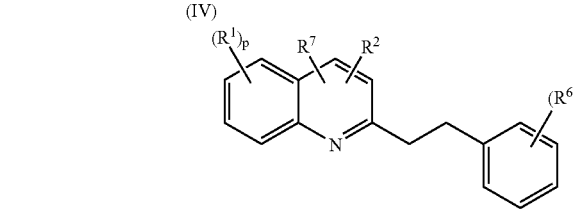

(II-a)

Intermediates of formula (IV) wherein $R^2$ and $R^7$ represent hydrogen, said intermediates being represented by formula (IV-a), can be prepared by reacting an intermediate of formula (V) with an intermediate of formula (VI) in the presence of a suitable base, such as for example sodium hydroxide.

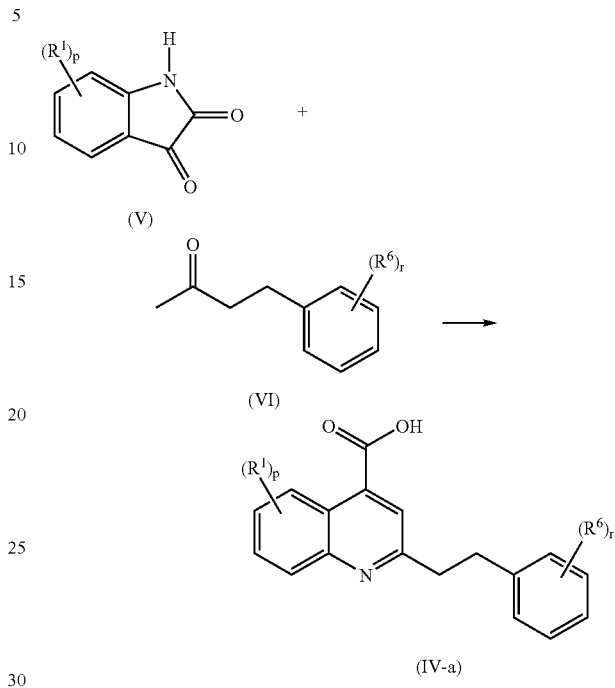

Intermediates of formula (II) wherein the

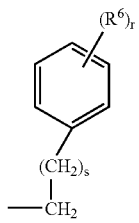

radical is placed in position 2 of the quinoline ring and s is 0, said intermediates being represented by formula (I-b), can be prepared by reacting an intermediate of formula (VII) wherein $W_1$ represents a suitable leaving group, such as for example halo, e.g. chloro and the like, with an intermediate of formula (VIII) wherein $W_2$ represents a suitable leaving group, such as for example halo, e.g. chloro, bromo and the like, in the presence of Zn, chlorotrimethylsilane, 1,2-dibromoethane and $Pd(PPh_3)_4$ and a suitable solvent such as for example tetrahydrofuran.

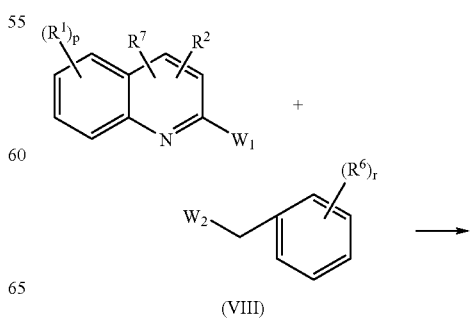

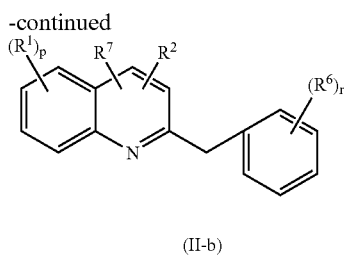

(II-b)

Intermediates of formula (VII) wherein $W_1$ represents chloro, said intermediates being represented by formula (VII-a), can be prepared by reacting an intermediate of formula (IX) with $POCl_3$.

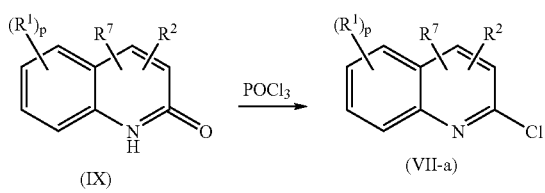

Intermediates of formula (IX) can be prepared by reacting an intermediate of formula (X) with 4-methylbenzenesulfonyl chloride in the presence of a suitable solvent, such as for example methylene chloride, and a suitable base, such as for example dipotassium carbonate.

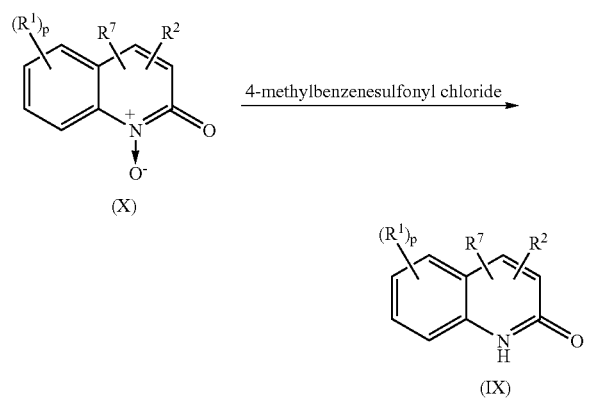

Intermediates of formula (X) can be prepared by reacting an intermediate of formula (XI) with a suitable oxidizing agent, such as for example 3-chlorobenzenecarboperoxoic acid, in the presence of a suitable solvent, such as for example methylene chloride.

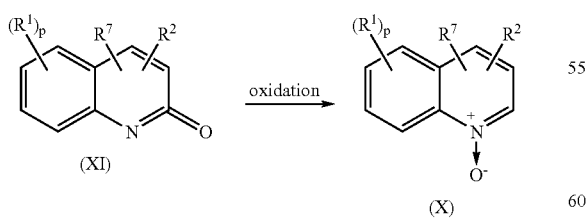

Intermediates of formula (II) wherein s is 0, said intermediates being represented by formula (II-c), can be prepared by reacting an intermediate of formula (XII) with $Et_3SiH$ in the presence of a suitable acid, such as for example trifluoroacetic acid, and a suitable solvent, such as for example methylene chloride.

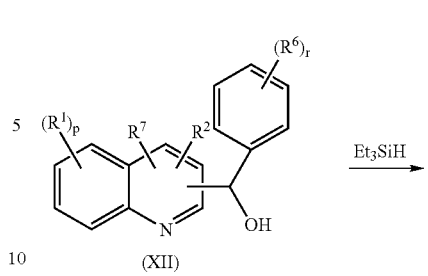

(II-c)

Intermediates of formula (XII) can be prepared by reacting an intermediate of formula (XIII) wherein $W_3$ represents a suitable leaving group, such as for example halo, e.g. chloro or bromo and the like, with an intermediate of formula (XIV) in the presence of a suitable coupling agent, such as for example n-butyl lithium, secBuLi, and in the presence of a suitable solvent, such as for example tetrahydrofuran, and optionally in the presence of a suitable base, such as for example 2,2,6,6-tetramethylpiperidine, $NH(CH_2CH_2CH_3)_2$, N,N-diisopropylamine or trimethylethylenediamine.

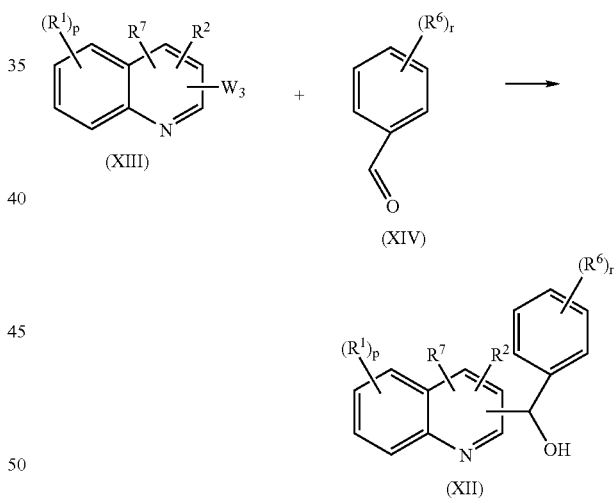

Intermediates of formula (XII) wherein the

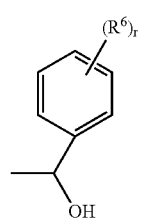

radical is placed in position 8 of the quinoline ring, $R^2$ is placed in position 2, $R^7$ is placed in position 4 and $R^1$ is placed in position 6 of the quinoline ring, said intermediates being represented by formula (XII-a), can be prepared by reacting an intermediate of formula (XV) with an intermediate of formula (XIV) in the presence of a suitable coupling agent, such as for example n-butyl lithium, secBuLi, and in the presence of a suitable solvent, such as for example tetrahydrofuran, and optionally in the presence of a suitable base, such as for example 2,2,6,6-tetramethylpiperidine, NH(CH$_2$CH$_2$CH$_3$)$_2$, N,N-diisopropylamine or trimethylethylenediamine.

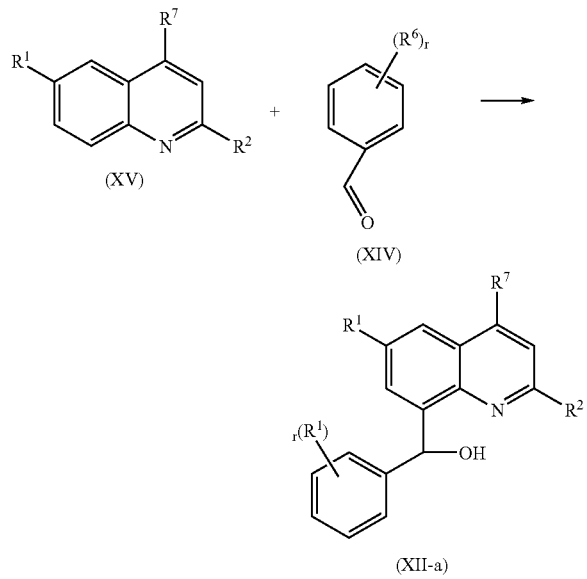

Intermediates of formula (III) are compounds that are either commercially available or may be prepared according to conventional reaction procedures generally known in the art. For example, intermediate compounds of Formula (III) wherein q is equal to 1, said intermediates being represented by formula (III-a), can be prepared according to the following reaction scheme (1):

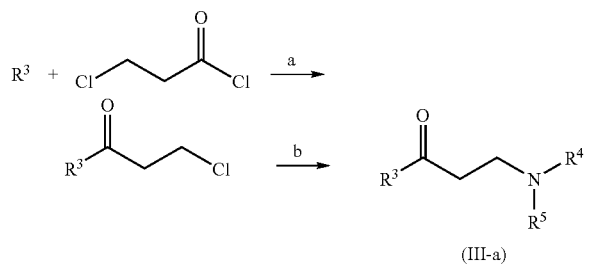

Reaction scheme (1) comprises step (a) in which an appropriate R$^3$ is reacted by Friedel-Craft reaction with an appropriate acylchloride such as 3-chloropropionyl chloride or 4-chlorobutyryl chloride, in the presence of a suitable Lewis acid, such as AlCl$_3$, FeCl$_3$, SnCl$_4$, TiCl$_4$ or ZnCl$_2$ and a suitable reaction-inert solvent, such as methylene chloride or ethylene dichloride. The reaction may conveniently be carried out at a temperature ranging between room temperature and reflux temperature. In a next step (b) an amino group (e.g. —NR$^4$R$^5$) is introduced by reacting the intermediate compound obtained in step (a) with an appropriate amine HNR$^4$R$^5$.

Intermediates of formula (III) can also be prepared by reacting an intermediate of formula (XVI) and an intermediate of formula (XVII) with formaldehyde in the presence of a suitable solvent, such as for example an alcohol, e.g. ethanol, and a suitable acid, e.g. HCl.

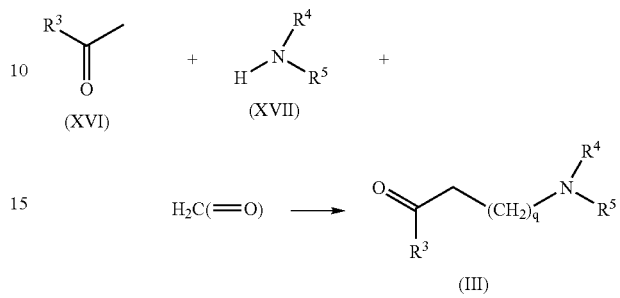

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC, chiral chromatography. Individual diastereoisomers or individual enantiomers can also be obtained by Supercritical Fluid Chromatography (SCF).

Intermediates of formula (XVIII) can be prepared by reacting first an appropriately substituted quinoline of formula (XIII) with an appropriately substituted deoxybenzoin in the presence of a suitable catalyst, such as for example palladium diacetate, a suitable ligand, such as for example X-PHOS, a suitable base, such as for example cesium carbonate, a suitable solvent, such as for example xylene, under N$_2$ flow (see step (a) in the scheme below). In a next step (b), the product obtained in step (a) is reacted with a suitable Grignard reagents (e.g. CH$_2$=CH—(CH$_2$)$_{q'}$—Mg—Br, such as for example allylmagnesium bromide, in a suitable solvent, such as for example tetrahydrofuran.

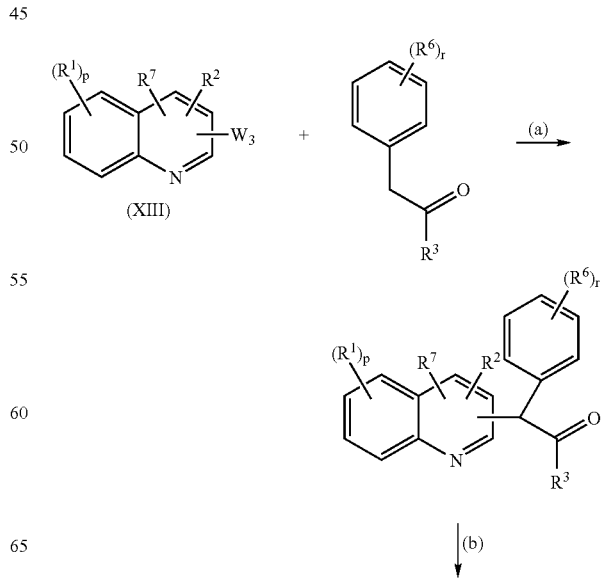

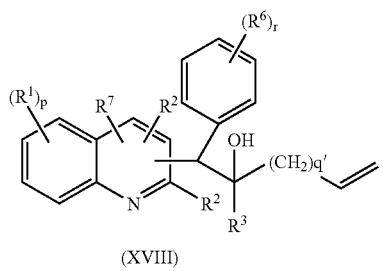

(XVIII)

The following examples illustrate the present invention without being limited thereto.

EXPERIMENTAL PART

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction.

In case "A" and "B" are stereoisomeric mixtures, in particular mixtures of diastereoisomers, they can be further separated whereby the respective first fractions isolated are designated "A1" respectively "B1" and the second as "A2" respectively "B2", without further reference to the actual stereochemical configuration. However, said "A1", "A2" and "B1", "B2" isomeric forms, in particular said "A1", "1" and "B1", "B2" enantiomeric forms, can be unambiguously characterized by a person skilled in the art, using art-known methods such as, for example, X-ray diffraction.

For the synthesis of the present compounds, reference is made to WO2005/075428, which is incorporated herein by reference.

Hereinafter, "DIPE" is defined as diisopropyl ether, "THF" is defined as tetrahydrofurane, "HOAc" is defined as acetic acid, "EtOAc" is defined as ethylacetate, Rt means retention time obtained in the LCMS method and is expressed in minutes.

A. Preparation of the Intermediate Compounds

Example A1

Preparation of Intermediate 1 and Intermediate 2

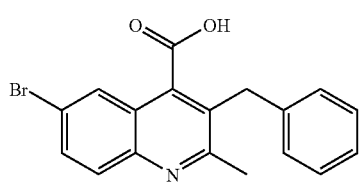

Intermediate 1

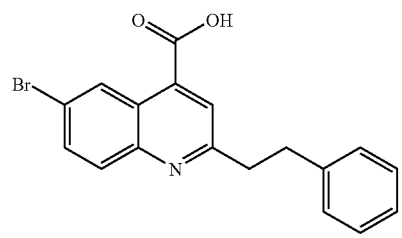

Intermediate 2

A mixture of 5-bromo-1H-indole-2,3-dione (0.221 mol) in NaOH 3N (500 ml) was stirred at 80° C. for 30 minutes and then cooled to room temperature. 4-Phenyl-2-butanone (0.221 mol) was added. The mixture was stirred and refluxed for 90 minutes, cooled to room temperature and acidified with HOAc until pH=5. The precipitate was filtered off, washed with $H_2O$ and dried. Yield: 75 g (95%) of a mixture of intermediate 1 and intermediate 2.

Example A2

Preparation of Intermediate 3

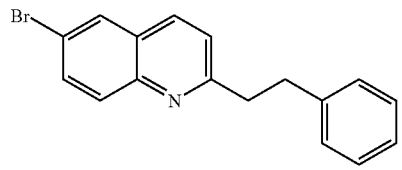 [SMILES: Brc1ccc2nc(CCc3ccccc3)ccc2c1]

A mixture of intermediate 1 and intermediate 2 (0.21 mol) in 1,1'-oxybis[benzene] (600 ml) was stirred at 300° C. for 12 hours. EtOAc was added. The mixture was extracted three times with HCl 6N, basified with $K_2CO_3$ solid and extracted with $CH_2Cl_2$. The organic layer was separated, dried ($MgSO_4$), filtered and the solvent was evaporated. The residue (36 g) was purified by column chromatography over silica gel (eluent: $CH_2Cl_2/CH_3OH$ 99/1; 15-40 µm). The pure fractions were collected and the solvent was evaporated. Yield: 11 g (16%) of intermediate 3.

Example A3

Preparation of Intermediate 4

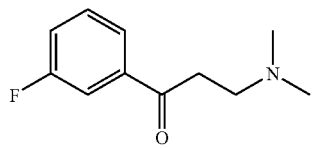

A mixture of 1-(3-fluorophenyl)ethanone (0.195 mol), formaldehyde (0.235 mol) and $NH(CH_3)_2.HCl$ (0.235 mol) in ethanol (300 ml) and HCl conc. (1 ml) was stirred and refluxed overnight, then brought to room temperature. The precipitate was filtered, washed with ethanol and dried. The mother layer was evaporated. The residue was taken up in diethyl ether. The precipitate was filtered, washed with diethyl ether and dried. This fraction was taken up in $K_2CO_3$ 10%. The precipitate was washed with CH₂Cl₂ and dried. Yield: 18.84 g (49%) of intermediate 4.

Example A4 a. Preparation of Intermediate 5

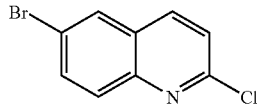 [SMILES: Clc1ccc2cc(Br)ccc2n1]

A mixture of 6-bromo-2(1H)-quinolinone (0.089 mol) in POCl₃ (55 ml) was stirred at 60° C. overnight, then at 100° C. for 3 hours and the solvent was evaporated. The residue was taken up in CH₂Cl₂, poured out into ice water, basified with NH₄OH concentrated, filtered over celite and extracted with CH₂Cl₂. The organic layer was separated, dried (MgSO₄), filtered and the solvent was evaporated. Yield: 14.5 g of intermediate 5 (67%).

b. Preparation of Intermediate 6

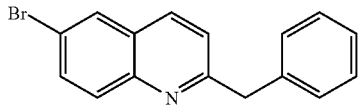 [SMILES: Brc1ccc2nc(Cc3ccccc3)ccc2c1]

A mixture of Zn (0.029 mol) and 1,2-dibromoethane (0.001 mol) in THF (6 ml) was stirred and refluxed for 10 minutes, then cooled to room temperature. Chlorotrimethylsilane (0.001 mol) was added. The mixture was stirred at room temperature for 30 minutes. A solution of bromomethylbenzene (0.025 mol) in THF (25 ml) was added dropwise at 5° C. for 90 minutes. The mixture was stirred at 0° C. for 2 hours. A solution of intermediate 5 (prepared according to A4.a) (0.021 mol) in THF (75 ml) was added. Pd(PPh₃)₄ (0.0008 mol) was added. The mixture was stirred and refluxed for 2 hours, then cooled to room temperature, poured out into NH₄Cl 10% and extracted with EtOAc. The organic layer was washed with H₂O, then with saturated NaCl, dried (MgSO₄), filtered, and the solvent was evaporated. The residue (12 g) was purified by column chromatography over silica gel (eluent: cyclohexane/CH₂Cl₂ 50/50; 20-45 μm). Two fractions were collected and the solvent was evaporated. Yield of the second fraction: 2.5 g of intermediate 6.

Example A5 a. Preparation of Intermediate 7

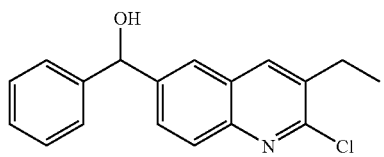 [SMILES: CCc1cc2cc(C(O)c3ccccc3)ccc2nc1Cl]

n-BuLi (1.6 M) (0.066 mol) was added dropwise at −50° C. to a mixture of 6-bromo-2-chloro-3-ethylquinoline (0.055 mol) in THF (150 ml). The mixture was stirred at −50° C. for 1 hour. A solution of benzaldehyde (0.066 mol) in THF (70 ml) was added at −70° C. The mixture was stirred at −70° C. for 1 hour, poured out into H₂O at 0° C. and extracted with EtOAc. The organic layer was separated, dried (MgSO₄), filtered, and the solvent was evaporated. The residue (15 g) was crystallized from DIPE/iPrOH. The precipitate was filtered off and dried. Yield: 7.6 g of intermediate 7 (46%).

b. Preparation of Intermediate 8

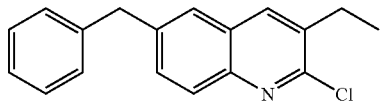 [SMILES: CCc1cc2cc(Cc3ccccc3)ccc2nc1Cl]

A mixture of intermediate 7 (prepared according to A5.a) (0.021 mol), Et₃SiH (0.21 mol) and CF₃COOH (0.21 mol) in CH₂Cl₂ (100 ml) was stirred at room temperature for 3 days. H₂O was added. The mixture was extracted with CH₂Cl₂. The organic layer was separated, washed with K₂CO₃ 10%, dried over magnesium sulfate, filtered and the solvent was evaporated. The residue (8 g) was purified by column chromatography over silica gel (eluent: cyclohexane/AcOEt 95/5; 15-40 μm). The pure fractions were collected and the solvent was evaporated. Yield: 3.8 g of intermediate 8 (64%, m.p.: 66° C.).

Example A6 a. Preparation of Intermediate 9

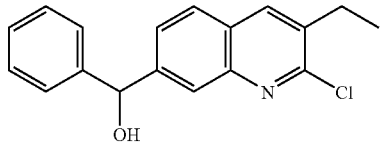 [SMILES: CCc1cc2ccc(C(O)c3ccccc3)cc2nc1Cl]

n-Butyl lithium (0.055 mol) was added slowly at −70° C. to a mixture of 7-bromo-2-chloro-3-ethylquinoline (0.037 mol) in THF (100 ml) under N₂ flow. The mixture was stirred for 2 hours, then a solution of benzaldehyde (0.055 mol) in THF (55 ml) was added. The mixture was stirred for 3 hours, water was added at −20° C. and the mixture was extracted with EtOAc. The organic layer was separated, dried over magnesium sulfate, filtered and the solvent was evaporated. The residue (12.2 g) was purified by column chromatography over silica gel (eluent: cyclohexane/AcOEt 80/20; 15-40 μm). The pure fractions were collected and the solvent was evaporated. Yield: 6.1 g of intermediate 9 (56%).

b. Preparation of Intermediate 10

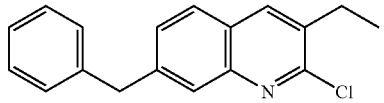 [SMILES: CCc1cc2ccc(Cc3ccccc3)cc2nc1Cl]

A mixture of intermediate 9 (prepared according to A6.a) (0.0205 mol), Et₃SiH (0.205 mol) and CF₃COOH (0.205 mol) in CH₂Cl₂ (300 ml) was stirred at room temperature for 7 days. H₂O was added. The mixture was extracted with CH₂Cl₂. The organic layer was separated, washed with K₂CO₃ 10%, dried over magnesium sulfate, filtered and the solvent was evaporated. The residue (7.1 g) was purified by column chromatography over silica gel (eluent: cyclohexane/AcOEt 95/5; 15-40 μm). The pure fractions were collected and the solvent was evaporated. Yield: 4.8 g of intermediate 10 (83%).

Example A7 a. Preparation of Intermediate 11

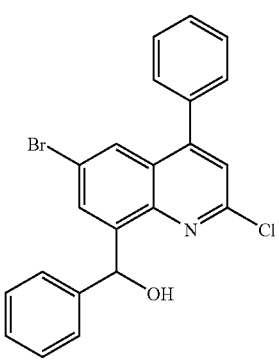 [SMILES: OC(c1ccccc1)c1cc(Br)cc2c(-c3ccccc3)cc(Cl)nc12]

n-Butyl lithium (0.0090 mol) was added slowly at −20° C. to a mixture of 2,2,6,6-tetramethylpiperidine (0.0090 mol) in THF (15 mL) under N₂ flow. The mixture was stirred for 20 minutes, then cooled to −70° C. A solution of 6-bromo-2-chloro-4-phenylquinoline (0.0060 mol) in THF (40 mL) was added. The mixture was stirred for 1 hour. A solution of benzaldehyde (0.0090 mol) in THF (15 ml) was added. The mixture was stirred for 1 hour at −70° C. then 3 hours at room temperature. H₂O was added. The mixture was extracted with EtOAc. The organic layer was separated, dried over magnesium sulfate, filtered and the solvent was evaporated. The residue (3.0 g) was purified by column chromatography over silica gel (eluent: cyclohexane/AcOEt: 95/5; 15-40 μm). The pure fractions were collected and the solvent was evaporated. Yield: 1.8 g of intermediate 11 (71%).

b. Preparation of Intermediate 12

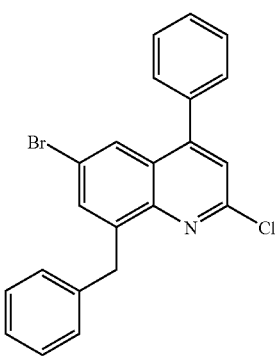 [SMILES: Clc1cc(-c2ccccc2)c2cc(Br)cc(Cc3ccccc3)c2n1]

A mixture of intermediate 11 (prepared according to A7.a) (0.0042 mol), Et₃SiH (0.0424 mol) and CF₃COOH (0.0424 mol) in CH₂Cl₂ (100 ml) was stirred at room temperature for 24 hours. H₂O was added. The mixture was extracted with CH₂Cl₂. The organic layer was separated, washed with K₂CO₃ 10%, dried over magnesium sulfate, filtered and the solvent was evaporated. The residue (1.3 g) was crystallized from DIPE. The precipitate was filtered off and dried. Yield: 0.66 g of intermediate 12 (38%, m.p.: 121° C.)

Example A8 a) Preparation of Intermediate 13

Intermediate 13

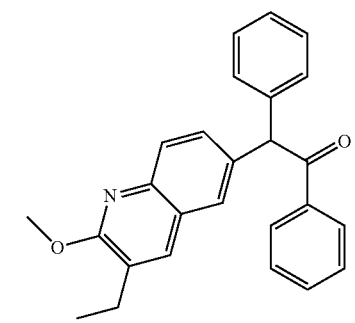

A mixture of deoxybenzoin (1 mmol),

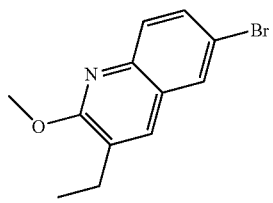

(1 mmol), XPHOS (0.08 mmol), palladium diacetate (0.04 mmol), cesium carbonate (2 mmol) in xylene (4 ml) was flushed with N₂ and heated at 145° C. for 20 hours. The reaction was cooled to room temperature and 2 ml of H₂O and 10 ml of CH₂Cl₂ were added. The layers were separated (Extralute) and the separated organic layer was concentrated in vacuo. The residue was purified by HPLC on RP with NH₄HCO₃-buffer. The product fractions were collected and the solvent was evaporated. Yield: intermediate 13.

b) Preparation of Intermediate 14

Intermediate 14

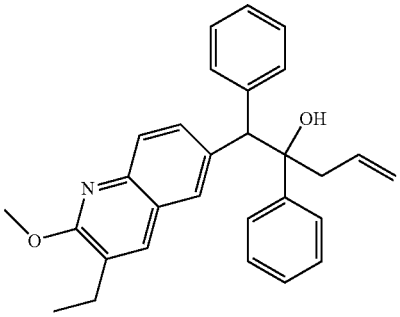

Intermediate 13 (0.000466 mol) was dissolved in THF (3 ml) and a solution of allylmagnesium bromide (1M in Et₂O, 1 mmol) was added. After stirring for 2 hours at room temperature, 2 ml saturated NH$_4$Cl solution was added and stirring was continued for 1 hour. The mixture was extracted with CH$_2$Cl$_2$, the layers were separated on extralute and the organic layer was concentrated in vacuo. The residue was purified by HPLC on RP with NH$_4$HCO$_3$-buffer. Yield: 0.053 g (17%) of intermediate 14.

B. Preparation of the Final Compounds

Example B1

Preparation of Compound 1 and Compound 4

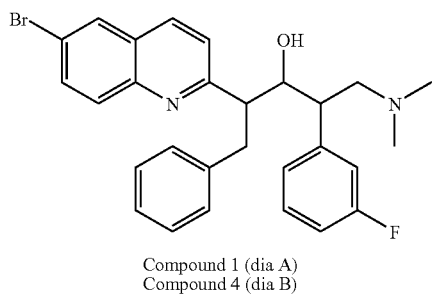 [SMILES: CN(C)CC(c1cccc(F)c1)C(O)C(Cc1ccccc1)c1ccc2cc(Br)ccc2n1]

Compound 1 (dia A)
Compound 4 (dia B)

n-BuLi 1.6M (0.0072 mol) was added at −20° C. to a mixture of N-(1-methylethyl)-2-propanamine.hydrochloride (1:1) (0.0071 mol) in THF (25 ml) under nitrogen stream. The mixture was stirred for 20 minutes then cooled to −70° C. A solution of intermediate 3 (0.0061 mol) in THF (5 ml) was added. The mixture was stirred for 2 hours. A solution of intermediate 4 (0.0061 mol) in THF (5 ml) was added at −70° C. The mixture was stirred at −70° C. for 3 hours. NH$_4$Cl 10% was added. The mixture was extracted with EtOAc. The organic layer was separated, dried (MgSO$_4$), filtered, and the solvent was evaporated. The residue (3.4 g) was purified by column chromatography over silica gel (eluent: CH$_2$Cl$_2$/CH$_3$OH/NH$_4$OH 97/3/0.1; 15-40 μm). Two fractions were collected and the solvent was evaporated. The first residue (0.9 g) was crystallized from diisopropyl ether. The precipitate was filtered off and dried. Yield: 0.49 g of compound 1 (diastereoisomer A) (m.p.: 136° C.). The second residue (0.79 g) was crystallized from diisopropyl ether. The precipitate was filtered off and dried. Yield: 0.105 g of compound 4 (diastereoisomer B) (m.p.: 179° C.).

Example B2

Preparation of Compound 2 and Compound 3

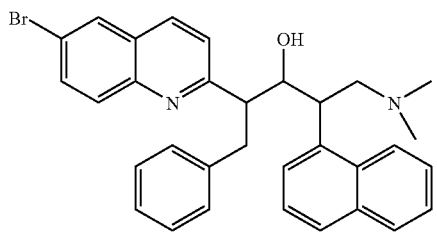

Compound 2 (dia A)
Compound 3 (dia B)

n-BuLi 1.6M (0.0072 mol) was added dropwise at −20° C. to a solution of N-(1-methylethyl)-2-propanamine.hydrochloride (1:1) (0.0071 mol) in THF (25 ml) under nitrogen stream. The mixture was stirred for 20 minutes. Then cooled to −70° C. A solution of intermediate 3 (0.0061 mol) in THF (5 ml) was added. The mixture was stirred for 2 hours. A solution of 3-(dimethylamino)-1-(1-naphthalenyl)-1-propanone (0.0062 mol) in THF (5 ml) was added at −70° C. The mixture was stirred at −70° C. for 3 hours. NH$_4$Cl 10% was added. The mixture was extracted with EtOAc. The organic layer was separated, dried (MgSO$_4$), filtered, and the solvent was evaporated. The residue (4 g) was purified by column chromatography over silica gel (eluent: CH$_2$Cl$_2$/CH$_3$OH/NH$_4$OH 97/3/0.1; 15-40 μm). Two fractions were collected and the solvent was evaporated. The first residue (0.61 g) was crystallized from DIPE. The precipitate was filtered off and dried. Yield: 0.303 g of compound 2 (diastereoisomer A) (m.p. 143° C.). The second residue (0.56 g) was purified by column chromatography over silica gel (eluent: CH$_2$Cl$_2$/CH$_3$OH 98/2). The pure fractions were collected and the solvent was evaporated. Yield: 0.104 g of compound 3 (diastereoisomer B) (m.p.: 69° C.).

Example B3

Preparation of Compound 5 and Compound 6

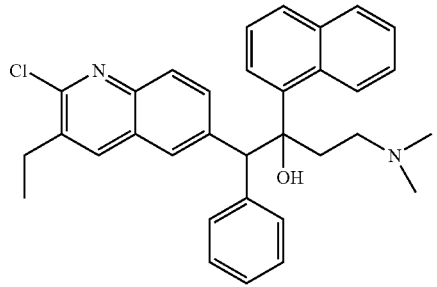

Compound 5 (dia A)
Compound 6 (dia B)

n-Butyl lithium (0.013 mol) was added slowly at −20° C. to a mixture of diisopropyl amine (0.013 mol) in THF (50 mL) under N$_2$ flow. The mixture was stirred for 20 minutes, then cooled to −70° C. A solution of intermediate 8 (0.0106 mol) in THF (20 mL) was added. The mixture was stirred for 1 hour. A solution of 3-(dimethylamino)-1-(1-naphthalenyl)-1-propanone (0.013 mol) in THF (10 mL) was added. The mixture was stirred for 2 hours. H$_2$O was added. The mixture was extracted with EtOAc. The organic layer was separated, dried over magnesium sulfate, filtered and the solvent was evaporated. The residue (5.5 g) was purified by column chromatography over silica gel (eluent: CH$_2$Cl$_2$/MeOH 99/1; 15-40 μm). Two fractions were collected and the solvent was evaporated. Yield: 0.33 g of compound 5 (diastereoisomer A) (3%, MH+=509, Rt: 5.46) and 0.11 g of compound 6 (diastereoisomer B) (1%, MH+=509, Rt: 5.58).

Following compound was prepared according to the above procedure. The purification of the residue (*) is indicated because different from the above-described purification.

| | | |
|---|---|---|
| compound 11 | The residue (5.4 g) was purified by ccolumn chromatography over silica gel (eluent: CH$_2$Cl$_2$/CH$_3$OH 98/2; 15-40 μm). The pure fractions were collected and the solvent was evaporated. Yield: 0.17 g of compound 13 (mixture of diastereoisomer A and diastereoisomer B: 45/55) (3%, MH+ = 495, Rt: 5.23). | 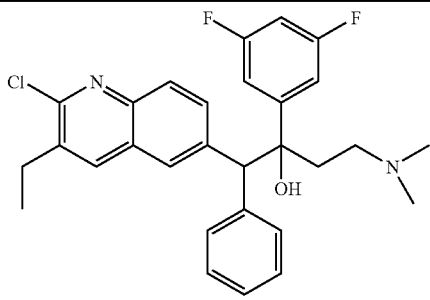<br>Compound 11 (A/B 45/55) |

Example B4

Preparation of Compound 7 and 8

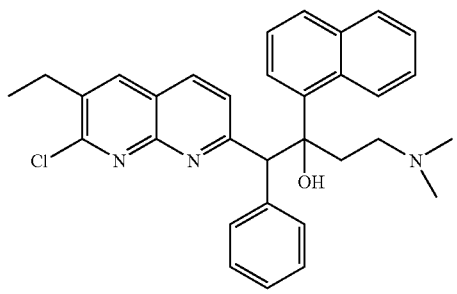

Compound 7 (diastereoisomer A)
Compound 6 (diastereoisomer B)

n-Butyl lithium (0.0043 mol) was added slowly at −20° C. to a mixture of diisopropyl amine (0.0043 mol) in THF (10 ml) under N$_2$ flow. The mixture was stirred for 20 minutes, then cooled to −70° C. A solution of intermediate 10 (prepared according to A6.b) (0.0036 mol) in THF (10 ml) was added. The mixture was stirred for 2 hours. A solution of 3-(dimethylamino)-1-(1-naphthalenyl)-1-propanone (0.0043 mol) in THF (10 ml) was added. The mixture was stirred for 2 hours. H$_2$O was added. The mixture was extracted with EtOAc. The organic layer was separated, dried over magnesium sulfate, filtered and the solvent was evaporated. The residue (*) (1.8 g) was purified by column chromatography over silica gel (eluent: CH$_2$Cl$_2$/MeOH/NH$_4$OH 98/2/0.2; 15-40 μm). Two fractions were collected and the solvent was evaporated. Yield: 0.17 g of fraction 1 and 0.15 g of fraction 2. Fraction 1 was crystallized from MeOH. The precipitate was filtered off and dried. Yield: 0.082 g of compound 7 (5%, diastereoisomer A). Fraction 2 was purified by column chromatography over silica gel (eluent: CH$_2$Cl$_2$/MeOH: 98/2; 15-40 μm). The pure fractions were collected and the solvent was evaporated. Yield: 0.13 g of compound 8 (7%, diastereoisomer B, MH+=509, Rt: 5.58).

Following compounds were prepared according to the above procedure. The purification of the residue (*) is indicated because different from the above-described purification.

| | | |
|---|---|---|
| compound 9 and compound 10 | The residue (1.9 g) was purified by column chromatography over silica gel (eluent: CH$_2$Cl$_2$/MeOH: 99/1; 15-40 μm). Two fractions were collected and the solvent was evaporated. Yield: Fraction 1: 0.42 g of diastereomer A and fraction 2: 0.31 g (18%) of compound 9 (diastereoisomer B, MH+ = 495, Rt: 5.8). Fraction 1 was crystallized from CH$_3$OH. The precipitate was filtered off and dried. Yield: 0.22 g of compound 10 (diastereoisomer A) (13%; m.p.: 185° C.) | 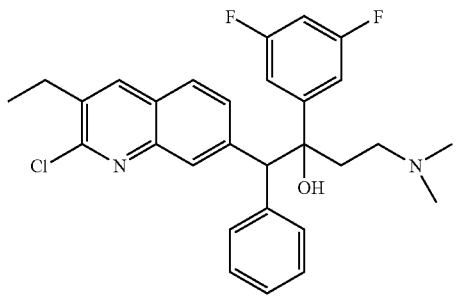<br>Compound 10 (diastereoisomer A)<br>Compound 9 (diastereoisomer B) |

Example B5

Preparation of Compound 12

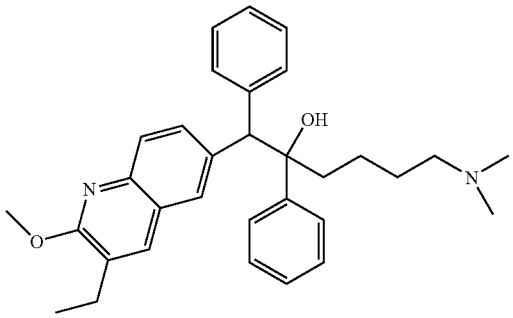

Compound 12

A mixture of intermediate 14 (0.000125 mol), dimethylamine (0.000125 mol), Rh(cod)$_2$BF$_4$ (0.000005 mol), Ir(cod)$_2$BF$_4$ (0.01 mmol), Xantphos (0.02 mmol) in THF (15 ml) and MeOH (15 ml) under CO (7 atm) and H$_2$ (33 atm) were heated in an autoclave at 100° C. for 48 hours. After cooling, the reaction mixture was concentrated in vacuo. The residue was dissolved in CH$_2$Cl$_2$ and the solution was filtered through a Silica SCX column (IST 530-0100-C) to catch the compound. The column was washed with CH$_2$Cl$_2$/MeOH: 90/10 and the product was released with CH$_2$Cl$_2$-MeOH/NH$_3$ 70/30. The solution was concentrated and the residue was purified by HPLC on RP with NH$_4$HCO$_3$-buffer. The product fractions were collected and the solvent was evaporated. Yield: compound 12 (dia A/dia B 19/81) (MH+=483, Rt: 6.42).

Compound 13 (dia A/dia B 35/65)

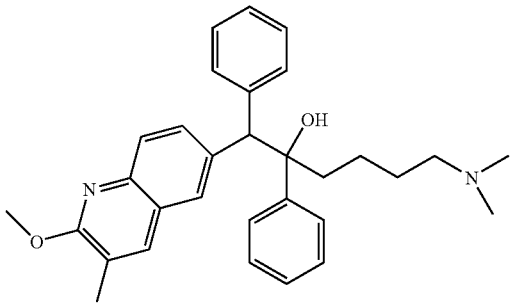

(MH+=469, Rt: 6.17) was prepared according to the protocol described above for compound 12.

C. Analytical Methods

The mass of the compounds was recorded with LCMS (liquid chromatography mass spectrometry). Three methods were used which are described below. The data are gathered in Table 1 below.

General Procedure A

The HPLC gradient was supplied by an Alliance HT 2795 (Waters) system consisting of a quaternary pump with degasser, an autosampler, and DAD detector. Flow from the column was split to the MS detector. MS detectors were configured with an electrospray ionization source. The capillary needle voltage was 3 kV and the source temperature was maintained at 100° C. on the LCT (Time of Flight-Z-spray mass spectrometer from Waters) and 3.15 kV and 110° C. on the ZQ (simple quadripole-Z-spray mass spectrometer from Waters). Nitrogen was used as the nebulizer gas. Data acquisition was performed with a Waters-Micromass MassLynx-Openlynx data system.

General Procedure B

The HPLC gradient was supplied by an Alliance HT 2790 (Waters) system consisting of a quaternary pump with degasser, an autosampler, a column oven (set at 40° C.) and DAD detector. Flow from the column was split to the MS detector. MS detectors were configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS—Method 1

In addition to general procedure A: LCMS analysis was carried out (electrospray ionization in positive mode, scanning mode from 100 to 900 amu) on a Kromasil C18 column (Interchim, Montluçon, FR; 5 µm, 4.6×150 mm) with a flow rate of 1 ml/minute. Two mobile phases (mobile phase A: 30% 6.5 mM ammonium acetate+40% acetonitrile+30% formic acid (2 ml/l); mobile phase B: 100% acetonitrile) were employed to run a gradient condition from 100% A for 1 minute to 100% B in 4 minutes, 100% B for 5 minutes to 100% A in 3 minutes, and reequilibrate with 100% A for 2 minutes.

LCMS—Method 2

In addition to general procedure A: LCMS analysis was carried out (electrospray ionization in both positive and negative (pulsed) mode scanning from 100 to 1000 amu) on a Kromasil C18 column (Interchim, Montluçon, FR; 3.5 µm, 4.6×100 mm) with a flow rate of 0.8 ml/minute. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute.

LCMS—Method 3

In addition to the general procedure B: Reversed phase HPLC was carried out on an Xterra MS C18 column (3.5 mm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 µl was used. Cone voltage was 10 V for positive ionization mode and 20 V for negative ionization mode.

TABLE 1

LCMS parent peak (MH+) and LCMS method used

| No. | MH+ | LCMS-method |
|---|---|---|
| Compound 7 | 509 | 1 |
| Compound 8 | 509 | 1 |
| Compound 9 | 495 | 2 |
| Compound 11 | 495 | 1 |
| Compound 5 | 509 | 1 |
| Compound 6 | 509 | 1 |

TABLE 1-continued

LCMS parent peak (MH+) and LCMS method used

| No. | MH+ | LCMS-method |
|---|---|---|
| Compound 12 | 483 | 3 |
| Compound 13 | 469 | 3 |

Pharmacological Examples

Preparation of Bacterial Suspensions for Susceptibility Testing

The bacteria used in this study were grown overnight in flasks containing 100 ml Mueller-Hinton Broth (Becton Dickinson—cat. no. 275730) in sterile de-ionized water, with shaking, at 37° C. Stocks (0.5 ml/tube) were stored at −70° C. until use. Bacteria titrations were performed in microtiter plates and colony forming units (CFUs) were determined. In general, an inoculum level of approximately 100 CFUs was used for susceptibility testing.

Anti Bacterial Susceptibility Testing: $IC_{90}$ Determination Microtitre Plate Assay Flat-bottom, sterile 96-well plastic microtiter plates were filled with 180 μl of sterile deionized water, supplemented with 0.25% BSA. Subsequently, stock solutions (7.8× final test concentration) of compounds were added in 45 μl volumes in column 2. Serial five-fold dilutions (45 μl in 180 μl) were made directly in the microtiter plates from column 2 to reach column 11. Untreated control samples with (column 1) and without (column 12) inoculum were included in each microtiter plate. Depending on the bacteria type, approximately 10 to 60 CFU per well of bacteria inoculum (100 TCID50), in a volume of 100 μl in 2.8× Mueller-Hinton broth medium, was added to the rows A to H, except column 12. The same volume of broth medium without inoculum was added to column 12 in row A to H. The cultures were incubated at 37° C. for 24 hours under a normal atmosphere (incubator with open air valve and continuous ventilation). At the end of incubation, one day after inoculation, the bacterial growth was quantitated fluorometrically. Therefore resazurin (0.6 mg/ml) was added in a volume of 20 μl to all wells 3 hours after inoculation, and the plates were re-incubated overnight. A change in colour from blue to pink indicated the growth of bacteria. The fluorescence was read in a computer-controlled fluorometer (Cytofluor Biosearch) at an excitation wavelength of 530 nm and an emission wavelength of 590 nm. The % growth inhibition achieved by the compounds was calculated according to standard methods. The $IC_{90}$ (expressed in μg/ml) was defined as the 90% inhibitory concentration for bacterial growth. The results are shown in Table 2.

Agar Dilution Method.

$MIC_{99}$ values (the minimal concentration for obtaining 99% inhibition of bacterial growth) can be determined by performing the standard Agar dilution method according to NCCLS standards* wherein the media used includes Mueller-Hinton agar.

* Clinical laboratory standard institute. 2005. Methods for dilution Antimicrobial susceptibility tests for bacteria that grows Aerobically: approved standard—sixth edition Time Kill Assays Bactericidal or bacteriostatic activity of the compounds may be determined in a time kill assay using the broth microdilution method *. In a time kill assay on *Staphylococcus aureus* and methicillin resistant *S. aureus* (MRSA), the starting inoculum of *S. aurues* and MRSA is $10^6$ CFU/ml in Muller Hinton broth. The antibacterial compounds are used at the concentration of 0.1 to 10 times the MIC (i.e. $IC_{90}$ as determined in microtitre plate assay). Wells receiving no antibacterial agent constitute the culture growth control. The plates containing the microorganism and the test compounds are incubated at 37° C. After 0, 4, 24, and 48 hrs of incubation samples are removed for determination of viable counts by serial dilution ($10^{-1}$ to $10^{-6}$) in sterile PBS and plating (200 μl) on Mueller Hinton agar. The plates are incubated at 37° C. for 24 hrs and the number of colonies are determined. Killing curves can be constructed by plotting the $\log_{10}$ CFU per ml versus time. A bactericidal effect is commonly defined as 3-$\log_{10}$ decrease in number of CFU per ml as compared to untreated inoculum. The potential carryover effect of the drugs is removed by serial dilutions and counting the colonies at highest dilution used for plating. No carryover effect is observed at the dilution of $10^{-2}$ used for plating. This results in limit of detection $5 \times 10^2$ CFU/ml or <2.7 log CFU/ml.

* Zurenko, G. E. et al. In vitro activities of U-100592 and U-100766, novel oxazolidinone antibacterial agents. *Antimicrob. Agents Chemother.* 40, 839-845 (1996).

Determination of Cellular ATP Levels

In order to analyse the change in the total cellular ATP concentration (using ATP bioluminescence Kit, Roche), assays are carried out by growing a culture of *S. aureus* (ATCC29213) stock in 100 ml Mueller Hinton flasks and incubate in a shaker-incubator for 24 hrs at 37° C. (300 rpm). Measure $OD_{405}$ nm and calculate the CFU/ml. Dilute the cultures to $1 \times 10^6$ CFU/ml (final concentration for ATP measurement: $1 \times 10^5$ CFU/100 μl per well) and add test compound at 0.1 to 10 times the MIC (i.e. $IC_{90}$ as determined in microtitre plate assay). Incubate these tubes for 0, 30 and 60 minutes at 300 rpm and 37° C. Use 0.6 ml bacterial suspension from the snap-cap tubes and add to a new 2 ml eppendorf tubes. Add 0.6 ml cell lysis reagent (Roche kit), vortex at max speed and incubate for 5 minutes at room temperature. Cool on ice. Let the luminometer warm up to 30° C. (Luminoskan Ascent Labsystems with injector). Fill one column (=6 wells) with 100 μl of the same sample. Add 100 μl Luciferase reagent to each well by using the injector system. Measure the luminescence for 1 sec.

TABLE 2

$IC_{90}$ values (μg/ml) determined according to the Microtitre plate assay

IC90 (μg/ml)

| Comp No. | STA 29213 | SPN 6305 | SPY 8668 | SMU 33402 | EFA 29212 | LMO 49594 | BSU 43639 | PAE 27853 | STA RMETHIC | STA 25923 | EFA 14506 |
|---|---|---|---|---|---|---|---|---|---|---|---|
| 5 | 12.8 | 12.8 | 12.8 | | 12.8 | 12.8 | 12.8 | 12.8 | 12.8 | 5.1 | 11.4 |
| 9 | 11.1 | 12.4 | 9.9 | 9.9 | 12.4 | 12.4 | 12.4 | 9.9 | 12.4 | 12.4 | 11.1 |
| 11 | 12.4 | 12.4 | 12.4 | | 12.4 | 7.9 | 39.3 | 12.4 | 49.5 | 49.5 | |
| 2 | 12.1 | 13.6 | 10.8 | 10.8 | 10.8 | 10.8 | 13.6 | 10.8 | 13.6 | 13.6 | 12.1 |

TABLE 2-continued

IC$_{90}$ values (μg/ml) determined according to the Microtitre plate assay

| Comp No. | STA 29213 | SPN 6305 | SPY 8668 | SMU 33402 | EFA 29212 | LMO 49594 | BSU 43639 | PAE 27853 | STA RMETHIC | STA 25923 | EFA 14506 |
|---|---|---|---|---|---|---|---|---|---|---|---|
| 10 | 12.4 | 12.4 | 12.4 |  | 12.4 | 12.4 | 12.4 | 9.9 | 12.4 | 12.4 |  |
| 1 | 12.8 | 12.8 | 10.1 | 10.1 | 12.8 | 10.1 |  | 12.8 | 12.8 | 12.8 |  |
| 6 | 12.8 | 12.8 | 12.8 |  | 12.8 | 12.8 | 12.8 | 12.8 | 50.9 | 12.8 | 11.4 |
| 8 | 12.8 | 12.8 | 12.8 |  | 12.8 | 12.8 | 12.8 | 12.8 | 12.8 | 12.8 |  |
| 13 | 7.43 | 7.43 |  |  |  |  |  |  |  |  |  |
| 12 | 1.53 | 1.53 |  |  |  |  |  |  |  |  |  |

BSU 43639 means *Bacillus subtilis* (ATCC43639); EFA 14506 means *Enterococcus faecalis* (ATCC14506); EFA 29212 means *Enterococcus faecalis* (ATCC29212); LMO 49594 means *Listeria monocytogenes* (ATCC49594); PAE 27853 means *Pseudomonas aeruginosa* (ATCC27853); SMU 33402 means *Streptococcus mutans* (ATCC33402); SPN 6305 means *Streptococcus pneumoniae* (ATCC6305); SPY 8668 means *Streptococcus pyogenes* (ATCC8668); STA 25923 means *Staphylococcus aureus* (ATCC25923); STA 29213 means *Staphylococcus aureus* (ATCC29213); STA RMETH means methicilline resistant *Staphylococcus aureus* (MRSA) (a clinical isolate from the University of Antwerp).
ATCC means American type tissue culture.

The invention claimed is:

1. A method for treating methicillin resistant *Staphylococcus aureus* (MRSA) bacterial infection in a mammal, said method comprising administering an effective amount of a compound of Formula (I) to said mammal:

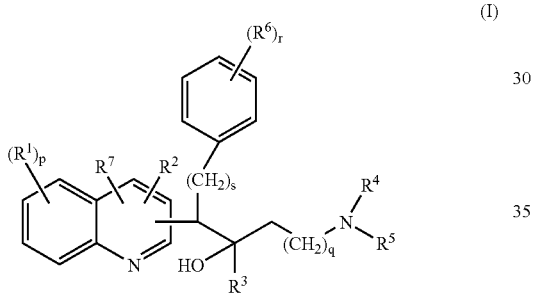

(I)

a pharmaceutically acceptable acid or base addition salt thereof, or a stereochemically isomeric form thereof wherein:

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2 or 3;

s is an integer equal to zero, 1, 2, 3 or 4;

$R^2$ is hydrogen; halo; alkyl; hydroxy; mercapto; alkyloxy optionally substituted with amino or mono or di(alkyl) amino or a radical of formula

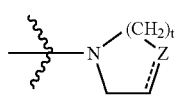

wherein Z is $CH_2$, CH—$R^8$, O, S, N—$R^8$ and t is an integer equal to 1 or 2 and the dotted line represents an optional bond; alkyloxyalkyloxy; alkylthio; mono or di(alkyl)amino wherein alkyl may optionally be substituted with one or two substituents each independently be selected from alkyloxy or Ar or Het or morpholinyl or 2-oxopyrrolidinyl; Ar; Het or a radical of formula

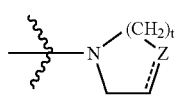

wherein Z is $CH_2$, CH—$R^8$, O, S, N—$R^8$; t is an integer equal to 1 or 2; and the dotted line represents an optional bond;

$R^3$ is alkyl, Ar, Ar-alkyl, Het or Het-alkyl;

q is an integer equal to zero, 1, 2, 3 or 4;

$R^4$ and $R^5$ each independently are hydrogen, alkyl or benzyl; or $R^4$ and $R^5$ together and including the N to which they are attached may form a radical selected from the group of pyrrolidinyl, 2-pyrrolinyl, 3-pyrrolinyl, pyrrolyl, imidazolidinyl, pyrazolidinyl, 2-imidazolinyl, 2-pyrazolinyl, imidazolyl, pyrazolyl, triazolyl, piperidinyl, pyridinyl, piperazinyl, pyridazinyl, pyrimidinyl, pyrazinyl, triazinyl, morpholinyl and thiomorpholinyl, each of said rings optionally being substituted with alkyl, halo, haloalkyl, hydroxy, alkyloxy, amino, mono- or dialkylamino, alkylthio, alkyloxyalkyl, alkylthioalkyl and pyrimidinyl;

$R^6$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^6$ radicals may be taken together to form together with the phenyl ring to which they are attached a naphthyl;

r is an integer equal to 1, 2, 3, 4 or 5; and $R^7$ is hydrogen, alkyl, Ar or Het;

$R^8$ is hydrogen, alkyl, hydroxyl, aminocarbonyl, mono- or di(alkyl)aminocarbonyl, Ar, Het, alkyl substituted with one or two Het, alkyl substituted with one or two Ar, Het-C(=O)— or Ar—C(=O)—;

alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with hydroxy, alkyloxy or oxo;

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, alkylcarbonyl, aminocarbonyl, morpholinyl and mono- or dialkylaminocarbonyl;

Het is a monocyclic heterocycle selected from the group of N-phenoxypiperidinyl, piperidinyl, pyrrolyl, pyrazolyl, imidazolyl, furanyl, thienyl, oxazolyl, isoxazolyl, thiazolyl, isothiazolyl, triazolyl, pyridinyl, pyrimidinyl, pyrazinyl and pyridazinyl; or a bicyclic heterocycle selected from the group of quinolinyl, isoquinolinyl, 1,2,3,4-tetrahydroisoquinolinyl, quinoxalinyl, indolyl, indazolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents, each substituent independently selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms or a cyclic saturated hydrocarbon radical having from 3 to 6 carbon atoms attached to a straight or branched saturated hydrocarbon radical having from 1 to 6 carbon atoms; wherein one or more carbon atoms are substituted with one or more halo atoms;

provided that radical

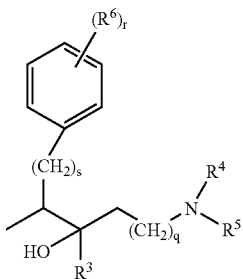

is bonded to one of positions 2, 6 or 7 of the quinoline moiety.

2. The method according to claim 1 wherein $R^1$ is hydrogen or halo.

3. The method according to claim 1 wherein p is equal to 1.

4. The method according to claim 1 wherein $R^2$ is hydrogen or halo.

5. The method according to claim 1 wherein $R^3$ is optionally substituted naphthyl or optionally substituted phenyl.

6. The method according to claim 1 wherein q is equal to 1 or 3.

7. The method according to claim 1 wherein $R^4$ and $R^5$ each independently are $C_{1-6}$alkyl.

8. The method according to claim 1 wherein $R^6$ is hydrogen.

9. The method according to claim 1 wherein $R^7$ is hydrogen or alkyl.

10. The method according to claim 1 wherein s is an integer equal to 0 or 1.

11. The method according to claim 1 wherein the bacterial infection is an infection with a gram-positive bacterium.

* * * * *